(12) United States Patent
Duvall et al.

(10) Patent No.: US 10,695,288 B2
(45) Date of Patent: Jun. 30, 2020

(54) REACTIVE OXYGEN SPECIES (ROS)-RESPONSIVE COMPOSITIONS AND METHODS THEREOF

(71) Applicant: VANDERBILT UNIVERSITY, Nashville, TN (US)

(72) Inventors: Craig L. Duvall, Nashville, TN (US); John R. Martin, Nashville, TN (US); Kristin P. O'Grady, Nashville, TN (US); Christopher E. Nelson, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/946,732

(22) Filed: Nov. 19, 2015

(65) Prior Publication Data

US 2016/0175265 A1 Jun. 23, 2016

Related U.S. Application Data

(60) Provisional application No. 62/081,999, filed on Nov. 19, 2014.

(51) Int. Cl.
*A61K 9/00* (2006.01)
*A61K 9/16* (2006.01)
*A61K 9/107* (2006.01)
*A61K 31/121* (2006.01)
*A61K 31/4468* (2006.01)

(52) U.S. Cl.
CPC ............ *A61K 9/0019* (2013.01); *A61K 9/107* (2013.01); *A61K 9/1641* (2013.01); *A61K 31/121* (2013.01); *A61K 31/4468* (2013.01)

(58) Field of Classification Search
CPC .............. A61K 31/121; A61K 31/4468; A61K 9/0019; A61K 9/107; A61K 9/1641
See application file for complete search history.

(56) References Cited

U.S. PATENT DOCUMENTS

| | | |
|---|---|---|
| 8,252,846 B2 | 8/2012 | Murthy et al. |
| 2010/0055189 A1* | 3/2010 | Hubbell ............... A61K 9/0034 |
| | | 424/489 |
| 2012/0164065 A1* | 6/2012 | Manganaro .......... A61K 9/0019 |
| | | 424/1.21 |
| 2015/0231302 A1 | 8/2015 | Duvall et al. |
| 2015/0283254 A1* | 10/2015 | Duvall ............. A61K 47/48176 |
| | | 424/78.29 |

FOREIGN PATENT DOCUMENTS

| WO | 2009140427 | 5/2009 |
|---|---|---|
| WO | 2009140421 | 11/2009 |
| WO | 2009140423 | 11/2009 |
| WO | 2009140429 | 11/2009 |
| WO | 2010053596 | 5/2010 |
| WO | 2014047524 | 3/2014 |
| WO | 2014066912 | 5/2014 |

OTHER PUBLICATIONS

Napoli A, Valentini M, Tirelli N, Muller M, Hubbell JA. Oxidation-responsive polymeric vesicles. Nat Mater. 2004;3:183-9.
Reddy ST, Rehor A, Schmoekel HG, Hubbell JA, Swartz MA. In vivo targeting of dendritic cells in lymph nodes with poly(propylene sulfide) nanoparticles. J Control Release. 2006;112:26-34.
Hu P. Tirelli N. Scavenging ROS: superoxide dismutase/catalase mimetics by the use of an oxidation-sensitive nanocarrier/enzyme conjugate. Bioconjugate Chem. 2012;23:438-49.
Velluto D, Demurtas D, Hubbell JA. PEG-b-PPS diblock copolymer aggregates for hydrophobic drug solubilization and release: cyclosporin A as an example. Mol Pharm. 2008;5:632-42.
Gupta MK, Meyer TA, Nelson CE, Duvall CL. Poly(PS-b-DMA) micelles for reactive oxygen species triggered drug release. J Control Release. 2012;162:591-8.
Gupta MK, Martin JR, Werfel TA, Shen T, Page JM, Duvall CL. Cell Protective, ABC triblock polymer-based thermoresponsive hydrogels with ROS-triggered degradation and drug release. J Am Chem Soc. 2014;136:14896-902.
Shahani K, Swaminathan SK, Freeman D, Blum A, Ma L, Panyam J. Injectable sustained release microparticles of curcumin: a new concept for cancer chemoprevention. Cancer Res. 2010;70:4443-52.

* cited by examiner

*Primary Examiner* — Snigdha Maewall
(74) *Attorney, Agent, or Firm* — Stites & Harbison PLLC; Sean P. Ritchie

(57) ABSTRACT

A reactive oxygen species savaging emulsion; the emulsion comprising an injectable pharmaceutically acceptable composition and a polymeric poly(propylene sulfide) microsphere for targeted delivery to a site with elevated reactive oxygen species. In embodiments of the present invention, the microsphere is loaded with a biologically active agent.

22 Claims, 15 Drawing Sheets

A)

REACTIVE OXYGEN SPECIES (ROS)-RESPONSIVE COMPOSITIONS AND METHODS THEREOF

GOVERNMENT INTEREST

This invention was made with government support under Grant No. R21 HL109748 awarded by the National Institutes of Health and Grant No. DGE-0909667 awarded by the National Science Foundation. The government has certain rights in the invention.

TECHNICAL FIELD

The presently-disclosed subject matter relates to reactive oxygen species (ROS)-responsive compositions and methods for using the same. In particular, the presently-disclosed subject matter relates to poly(propylene sulfide) (PPS) particles and therapeutic methods for using the same. Embodiments of the present invention include local, sustained, and "on-demand" drug delivery.

INTRODUCTION

Elevated levels of reactive oxygen species (ROS) cause oxidative stress that contributes to inflammation-related pathologies such as peripheral arterial disease (PAD) [1-3]. Under pathological conditions, leukocytes that are recruited to inflamed sites produce and then release an excess of ROS, causing harm to the surrounding tissues through DNA damage and lipid peroxidation [1, 3, 4]. This process is self-propagating, as the ROS released by inflammatory cells can increase the expression of leukocyte adhesive factors on the endothelium, resulting in local extravasation of additional leukocytes that produce additional ROS [5, 6]. Diabetic patients are especially susceptible to oxidative stress and inflammatory diseases, because excessive glucose increases expression of endothelial cell nitric oxide synthase (eNOS) and the production of superoxide, leading to increased generation of hydroxyl radicals, hydrogen peroxide, and peroxynitrite [7-9]. In diabetes, there is a chronic pro-inflammatory environment, where ROS contributes to both endothelial dysfunction and a predisposition to PAD [9, 10]. The strong relationship between hyperglycemia, oxidative stress, and microvascular complications is also supported by observations that compared to the general population, diabetic patients have a four times greater risk of developing PAD [11], worse lower-extremity function [12], and a greater risk of amputation [13, 14]. Furthermore, preclinical studies have shown that animals with type 1 diabetes have an impaired vascular response to ischemia [15-17] and that decreasing oxidative stress improves post-ischemic neovascularization [15, 16]. Therefore, therapeutics that locally reduce oxidative stress have significant potential for treatment of inflammatory diseases like diabetic PAD.

Curcumin, a natural molecule derived from turmeric, is a pleiotropic anti-inflammatory and antioxidant agent that acts through inhibiting the pro-inflammatory transcription factor nuclear factor kappa B (NF-κB) [18, 19] and by scavenging oxidative free radicals through H-atom donation and/or electron transfer [20]. These therapeutic effects would be beneficial for treatment of PAD in the context of chronic, diabetes-induced oxidative stress, and curcumin has shown promise in preclinical ischemia/reperfusion studies [21, 22]. However, therapeutic use of curcumin is limited due to its extreme hydrophobicity which reduces absorption and leads to rapid metabolism and elimination [23]. One approach to overcoming the poor aqueous solubility and stability of curcumin for clinical applications is to deliver it locally from a depot [24]. In order to improve bioavailability of curcumin, sustained/targeted delivery approaches including hydrogels [24], exosomes [25], and stimuli-responsive nanoparticles [4] have been pursued. Microparticles comprising hydrophobic, biodegradable polymers also offer a useful approach for creating an injectable, local depot for controlled drug release [26]. However, conventionally used PLGA-based microparticles are degraded by non-specific hydrolysis and produce acidic degradation products that can exacerbate local inflammation [27] and activate autocatalytic degradation of the particles [28]. This autocatalytic degradation leads to an uncontrolled drug release profile that limits the effectiveness of these particles as vehicles for sustained drug release.

Hence, there remains a need for compositions that reduce oxidative stress for the treatment of, for example, inflammatory diseases. There also remains a need for delivery vehicles that can carry and achieve a controlled release of certain substances, including hydrophobic substances, to a site of oxidative stress.

Embodiments of the present invention provide for a method for delivery of hydrophobic drugs from injectable microparticles to target the oxidative stress that contributes to inflammation-related pathologies. The particles we have developed are biodegradable, ROS-responsive, and preferentially targeted to inflammatory, phagocytic cell types. The hydrophobicity of PPS makes it a good candidate for efficient encapsulation of hydrophobic drugs. After delivery in vivo, exposure of PPS to ROS causes it to transition to a hydrophilic form, which triggers gradual particle swelling/dissolution and "on-demand" drug release. The reaction of PPS with ROS that triggers this phase change from hydrophobic to hydrophilic gives PPS "ROS sponge" function, which may also give the microparticles an inherent ability to help to "detoxify" oxidative stress and provide a cell protective effect (independent from any drug loaded into them), To confirm this ROS-responsiveness, we have shown that the in vitro rate of release of a hydrophobic drug from PPS microparticles is modulated by environmental levels of ROS such as hydrogen peroxide and peroxynitrite. The micron size of the particles allows for them to be retained at the tissue site as a stable, local depot for on-demand delivery, and the degradation products do not acidify the local environment. In fact, the present inventors have shown that the polymer itself improves cell survival in vitro in the presence of cytotoxic levels of hydrogen peroxide, and it has inherent therapeutic properties as an ROS scavenger both in vitro and in vivo. The present inventors have also demonstrated that the PPS microparticles improved bioavailability and therapeutic efficacy of an antioxidant and anti-inflammatory hydrophobic drug which exacerbates ROS levels in inflamed tissue when delivered in its free form. The size of the microparticles is tunable to some degree, but in the prior studies we have tuned the size to be around 1 micron which helps to target the particles to activated inflammatory cells. Without being bound by theory or mechanism, the present inventors envision that there is a combination of retention and drug release in the extracellular environment and a concentration of the particles within activated inflammatory cells (the particles are too big to be readily phagocytosed by other "normal" cell types). Data were obtained using the oil-in-water (O/W) microparticle fabrication method which enables encapsulation of hydrophobic cargo. However, this technology could also be extended for encapsulation of hydrophilic drug cargo using and water-in-oil-in-water (W/O/W) emulsion process.

PPS has previously been used in nanoparticle formats (and more recently by us in a hydrogel format). It is known that conversion of the hydrophobic sulfide to sulfoxides/sulfones causes a solubility change. The novelty of this invention is four-fold (1) fabrication of PPS into micron sized particles and fabrication of PPS particles almost exclusively utilize PLGA. (2) Application of this system for oxidation-responsive, "on-demand" delivery of a hydrophobic drug that combats inflammation, ROS, etc. Other reports have not focused/leveraged ROS responsiveness of the material to "smartly" modulate drug release. (3) The present inventors are also the first that we are aware of to demonstrate that the PPS polymer in itself provides potential therapeutic benefit, and we have shown this both in vitro and in vivo. Other delivery systems are solely effective for delivery of encapsulated drug and their degradation products can be inflammatory. (4) Finally, the size of the particles (~1 μm) enables formation of a local depot within the tissue stroma. Prior work with PPS has focused on nano-sized particles which are more likely to diffuse away. The size range of 1-5 microns also enables preferential uptake by the inflammatory cells that are the primary producers of damaging ROS.

BRIEF DESCRIPTION OF THE DRAWINGS

A better understanding of the features and advantages of the presently-disclosed subject matter will be obtained by reference to the following detailed description that sets forth illustrative embodiments as well as the Figures described below.

FIG. 2A) In vitro release of curcumin from PPS microspheres exposed to temporally-constant $H_2O_2$ concentrations ranging from 0 mM to 3 wt % (882 mM) showed $H_2O_2$ dose-dependent release. FIG. 2B) In vitro release of curcumin from PPS microspheres with intermittent exposure to 0.1 mM, 1 mM, and 2 mM SIN-1 showed SIN-1 dose-dependent, on demand release during temporal phases when SIN-1 was present. n=3 for all samples.

FIG. 4A) Confocal microscopy revealed that curcumin-PPS microspheres were internalized to a greater degree by LPS/IFN-γ stimulated RAW cells relative to non-activated macrophages and fibroblasts, suggesting size dependent targeting of the microparticles to pro-inflammatory macrophages. Scale bar is 20 Inset in stimulated RAW macrophages is the center slice of a z-stack, confirming cell internalization of microspheres. Inset scale bar is 5 FIG. 4B) Quantitative analysis of microsphere uptake was performed using flow cytometry to measure intracellular curcumin fluorescence, and significant differences were observed between all groups (p<0.05). FIG. 4C) Intracellular ROS levels are reduced in LPS/IFN-γ-stimulated RAW macrophages by treatment with PPS microspheres and Cur-PPS microspheres (p<0.05). Intracellular ROS levels in activated macrophages treated with CUR-PPS microspheres were statistically equivalent to the non-activated RAW cells. FIG. 4D) Secretion of MCP-1 is reduced in LPS/IFN-γ-stimulated RAW macrophages by treatment with Cur-PPS microspheres relative to blank PPS microspheres (p<0.05). Microsphere doses contain 3.4 μM curcumin or the equivalent polymer dose. *p<0.05 for differences between indicated groups. # p<0.05 relative to unstimulated macrophages (LPS/IFN-γ(−)/NT group).

FIG. 5A) Curcumin-PPS microspheres release curcumin more rapidly in the ischemic limb in comparison to the control limb. FIG. 5B) ROS levels in the gastrocnemius muscle are increased at day 1 post-surgery (level of ROS is 2.3-fold greater in ischemic versus control gastrocnemius). FIG. 5C) Blank PPS microspheres and curcumin-loaded PPS microspheres significantly reduce ROS in gastrocnemius muscles extracted from ischemic limbs. Data presented as mean±SEM. Saline group n=8, blank PPS group n=11, curcumin-PPS group n=10. *p<0.05 relative to saline treatment.

FIG. 6A) Representative images from the time course of hemoglobin oxygen saturation recovery from each treatment group delivered to the ischemic limb of diabetic mice. FIG. 6B) Hemoglobin saturation is significantly increased in the curcumin-PPS treated group (n=10) relative to the blank PPS (n=11) and saline-treated (n=8) groups over the time course of ischemic recovery. At day 2, the curcumin PPS group has a significantly higher hemoglobin saturation ratio compared to the saline group. Data presented as mean±SEM. *Cur-PPS group is significantly different from PPS and Saline groups over the time course from day 2 to 6 (p<0.05). PPS and Saline groups are not significantly different (p>0.9). # Cur-PPS and Saline differ significantly (p<0.05).

FIG. 7A) Representative images of vessel morphology from each treatment group. Scale bar is 1 mm. FIG. 8B) Curcumin-PPS treated mice had a significant increase in length of vasculature with diameters between 25 μm and 125 μm relative to the blank PPS microsphere group (p<0.05).

FIG. 10A) Free tempo-benzoate and tempo-PPS microspheres significantly reduce fluorescence from oxidized DHE relative to no treatment and blank PPS microspheres in a superoxide-generating system containing xanthine and xanthine oxidase (one-way ANOVA p<0.0001, *significant post-hoc comparison). FIG. 10B) Blank PPS microspheres significantly reduce Amplex Red fluorescence in a superoxide and $H_2O_2$-producing xanthine/xanthine oxidase system. Tempo-benzoate treatment significantly increases Amplex Red fluorescence as the superoxide in the system is converted to $H_2O_2$ (one-way ANOVA p<0.001, *significant post-hoc comparison relative to no treatment). Data presented as mean±SD.

FIG. 12A) Younger diabetic mice have a significant increase in HbSat relative to age-matched, non-diabetic mice that peaks at day 14 and is followed by regression. FIG. 12B) In older diabetic mice, there is no overshoot response in the HbSat ratio, and mice with 15 weeks of diabetes only differ significantly at day 14. FIG. 12C) The overshoot response in younger diabetic mice is also apparent in perfusion measurements, with significantly higher ratios at days 7, 14, and 28. FIG. 12D) In the older cohort of mice, there are no significant differences in perfusion ratio between the diabetic and non-diabetic groups. n=3/group for younger cohort and n≥6/group for older cohort. *p<0.05 relative to non-diabetic group at a given time point. †p<0.05 between 15-week diabetic mice and 5-week diabetic mice at day 14.

FIG. 14A) In the younger cohort, diabetic mice had significantly greater $H_2O_2$ in the gastrocnemius muscle compared to the non-diabetic group at day 8 post-surgery. FIG. 14B) In the older cohort, the mice with 15 weeks of diabetes had a greater increase in relative $H_2O_2$ levels in the gastrocnemius muscle compared to non-diabetic mice at day 14 post-surgery. Additionally, $H_2O_2$ is elevated in the ischemic limb relative to the control limb (ischemic/control ratio>1) in both muscles in both the non-diabetic and diabetic mice in the older cohort. n≥4/group for both cohorts. *p<0.05.

FIG. 16A) The high dose of PPS and tempo-PPS microspheres significantly reduced relative $H_2O_2$ levels in the gastrocnemius muscle at day 14 relative to saline-treated controls (p<0.05 for Kruskal-Wallis ANOVA and * indicates significant differences for post-hoc comparisons). FIG. 16B) At the functionally therapeutic dose of microspheres, no significant differences between treatment groups were detectable with the Amplex Red assay for fresh tissue excised at day 8. n=3-4/group for high dose and n=7-8/group for therapeutic.

FIG. 17A) Individual time point analyses did not identify significant differences between treatment groups in the HbSat response. FIG. 17B) At day 14, perfusion in the tempo-PPS group is significantly greater than that in the free tempo group as determined by a Kruskal-Wallis ANOVA (*p<0.05) with a post-hoc multiple comparisons test. n=15-20/group for days 0-7 and n=6-7/group for days 14-28.

DESCRIPTION OF EXEMPLARY EMBODIMENTS

Figure 1:
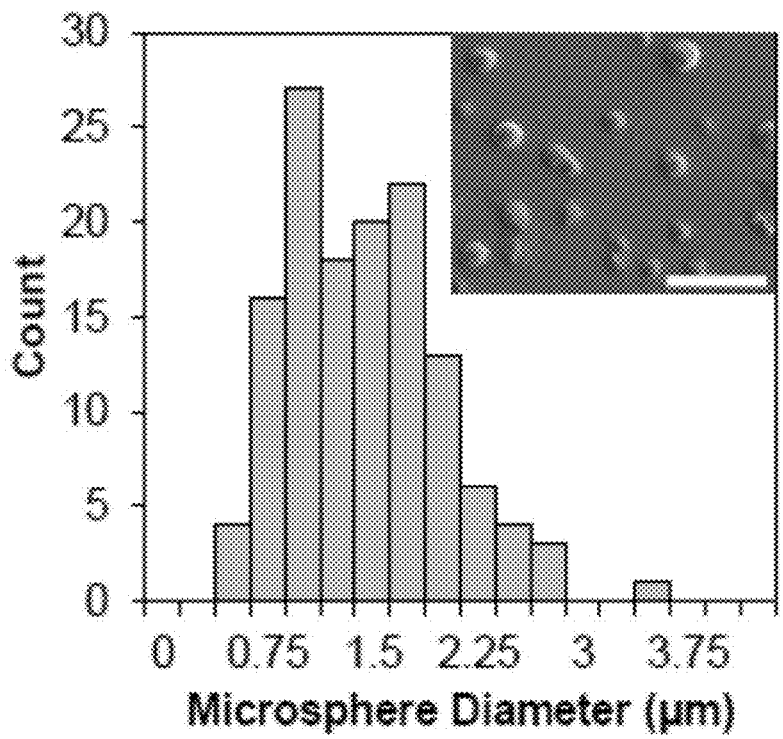
FIG. 1: The size distribution of curcumin-PPS microspheres, as analyzed by SEM, indicated that average microparticle diameter was 1.33 μm with a standard deviation of 0.55 μm. Scale bar is 10 μm.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compositions that are responsive to reactive oxygen species (ROS). In some embodiments the presently-disclosed subject matter relates to ROS-responsive particles that are comprised of poly(propylene sulfide) (PPS) that can be loaded with one or more bioactive agents. Indeed, in some embodiments the present particles can provide a sustained release of one or more bioactive agents, wherein the release is responsive to local ROS levels. Thus, the present particles can release bioactive agents based on environmental demand, and the degradation products do not acidify the local environment. Accordingly, the presently-disclosed ROS-responsive can be utilized in methods of treatment, including methods for treating inflammatory diseases, such as peripheral arterial disease and osteoarthritis, and other conditions that give rise to increased ROS in a subject.

In this regard, in embodiments of particles comprised of PPS, the PPS provides a ROS-scavenging quality to the particles. Relative to other known vehicles that are comprised of PPS, the present particles can further be sized for improved retention in tissue and uptake by phagocytic, ROS-producing cell types. The resulting particles can provide oxidation-responsive, "on-demand" delivery of a bioactive agent, including hydrophobic bioactive agents. In some embodiments the bioactive agents can combat inflammation, ROS, and the like. On the other hand, other known delivery mechanisms do not possess the same level of ROS responsiveness of the present particles.

The term "particle" as used herein, refers to particles that generally can be measured on a nanometer and/or micrometer scale. For example, in some embodiments the particles include a diameter of about 1 nm to about 999 nm in diameter. In other embodiments the particles include a diameter of about 1 μm to about 10 μm, including about 1 μm, 2 μm, 3 μm, 4 μm, 5 μm, 6 μm, 7 μm, 8 μm, 9 μm, or 10 μm. Thus, the term "particle" as used herein refers to the characteristics, and particularly the size, of a bioactive agent vehicle. In this regard, the term "particle" be used interchangeably with the terms "microsphere," "microparticle," and the like herein. In some instances, the size of the particles (e.g., about 1 μm) enables formation of a local depot within the tissue stroma, whereas in some instances nano-sized particles may be more likely to diffuse away. In some instances the size range of about 1 to about 5 microns also enables preferential uptake by the inflammatory cells that are the primary producers of damaging ROS.

As described herein, the present particles can be used to treat diseases and conditions that give rise to elevated ROS levels. Inflammation can increase levels of ROS, such as superoxide, hydrogen peroxide, and hydroxyl radicals, and/or nitric oxide (NO). Consequently, in some embodiments the particles and/or the biologically active agent delivered by the particles can reduce, inhibit, or relieve the symptoms associated with an inflammatory response. In particular, the particles and/or the biologically active agent can reduce, inhibit, or eliminate ROS and/or NO at a particular site.

The terms "biologically active agent," "bioactive agent," and the like are used herein to generally refer to any agent that can enhance, inhibit, promote, initiate, accelerate, active, inactive, or otherwise affect biological and/or chemical events in a subject. In some embodiments the biologically active agent is selected from the group consisting of enzymes, organic catalysts, antibiotics, antioxidants, anti-reactive oxygen species (ROS) agents, anti-inflammatories, proteins, glycoproteins, peptides, polyamino acids, antibodies, epitopes of antibodies, nucleic acids, steroidal molecules, antivirals, antirejection agents, immunosuppressants, cytokines, carbohydrates, pharmaceuticals, cells, viruses, single chain fragments, siRNA, miRNA (e.g., against the p53/MAP kinase pathway, etc.), virus vectors, prions, anti-proliferative agents (e.g., chemotherapeutics), anti-migratory agents, biologically active polymers (e.g., PPS), and combinations thereof. In some embodiments the biologically active agent is curcumin. In some embodiments the PPS particles themselves include therapeutic qualities. Loading such particles with bioactive agents can further enhance such therapeutic benefits.

As described herein, embodiments of the present particles can be prepared using an emulsion technique. Those of ordinary skill will recognize emulsion techniques for making the present particles upon reviewing this disclosure. Additionally, the examples provided herein provide specific, non-limiting examples of emulsion techniques for making the present particles.

Furthermore, embodiments of the presently-disclosed subject matter include pharmaceutical compositions comprising the isolated peptide and a pharmaceutically acceptable carrier. The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants and excipients. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like.

Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

Further still, the presently-disclosed subject matter includes methods for treating a subject. In some embodiments the subject has a disease or condition that gives rise to elevated ROS levels, such as peripheral arterial disease and osteoarthritis. In some embodiments the method comprises administering a composition that includes an embodiment of the present particles to the subject.

The term "administering" refers to any method of providing an isolated peptide, composition thereof, and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, intravitreous administration, intracameral (into anterior chamber) administration, subretinal administration, sub-Tenon's administration, peribulbar administration, administration via topical eye drops, and the like. Administration can be continuous or intermittent. In various aspects, a preparation can be administered therapeutically; that is, administered to treat an existing disease or condition (e.g., exposure to OP compounds). In further various aspects, a preparation can be administered prophylactically; that is, administered for prevention of a disease or condition.

Also, the term "subject" is inclusive of both human and animal subjects. Thus, veterinary uses are provided in accordance with the presently disclosed subject matter and the presently-disclosed subject matter provides methods for preventing oxidative damage in mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In this regard, the terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative (prophylactic) treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

EXAMPLES

The presently-disclosed subject matter is further illustrated by the following specific but non-limiting examples set forth below. These examples may include compilations of data that are representative of data gathered at various times during the course of development and experimentation related to the presently-disclosed subject matter.

Example 1

This Example demonstrates an aspect of the present invention, specifically related to targeting oxidative stress and inflammation in ischemic tissue, demonstrating the ability to improve neovascularization associated with diabetes.

2. Materials and Methods 2.1 Materials

All chemicals were purchased from Sigma-Aldrich (St. Louis, Mo., USA) and used as received unless otherwise described. Curcumin (368.38 g/mol; ≥94% curcuminoid content) was obtained from Sigma. Propylene sulfide was purchased from Acros Organics (NJ, USA) and purified by distillation just before polymerization. 87-90% hydrolyzed poly(vinyl alcohol) (PVA) of average molecular weight 30,000-70,000 was prepared into a 1% w/v solution in deionized water. Transwell inserts with 0.4 µm pore polycarbonate membranes (Corning, Lowell, Mass., USA) were used in 24 well plates for curcumin release experiments. SIN-1 was purchased from Invitrogen (San Diego, Calif., USA) as a package of 1 mg vials. Cell culture reagents, including fetal bovine serum (FBS), Dulbecco's Modified Eagle Medium (DMEM), and penicillin-streptomycin (p-s) were supplied by Gibco Cell Culture (Carlsbad, Calif., USA). 4-Cyano-4-(ethylsulfanyltiocarbonyl) sulfanylpentanoic acid (ECT) was synthesized following the previously reported procedure [40].

2.2 Microsphere Synthesis and Characterization 2.2.1 Synthesis of Polypropylene Sulfide) (PPS)

To prepare PPS as previously described [34, 41], propylene sulfide (3.16 mL, 40.4 mmol), ECT (52 mg, 0.20 mmol), TPPCl (tetraphenylphosphonium chloride-$Ph_4P^+Cl^-$) (14.9 mg, 0.040 mmol), and dry NMP (N-methyl pyrolidone) (10 mL) were placed in a dry glass ampoule equipped with a magnetic stirring bar, and the solution was degassed by three freeze-evacuate-thaw cycles. The reaction mixture was stirred at 60° C. for 20 hours, and the resulting polymer was purified by precipitation twice into a large excess of methanol and dried at 60° C. under vacuum to yield a red/yellow polymer oil. $^1$H-NMR ($CDCl_3$, 400 MHz): =1.25-1.45 (s, $CH_3$), 2.5-2.7 (m, CH), 2.85-3.0 (m, —$CH_2$).

2.2.2 Characterization of PPS

PPS was characterized for molecular weight and polydispersity by gel permeation chromatography (GPC, Agilent Technologies, Santa Clara, Calif., USA), and the chemical structure of the polymer was also analyzed by $^1$H NMR spectra recorded in $CDCl_3$(Brüker 400 MHz spectrometer). Molecular weight was measured using GPC with DMF+0.1 M LiBr mobile phase at 60° C. through three serial Tosoh Biosciences TSKGel Alpha columns (Tokyo, Japan). An Agilent refractive index (RI) detector and a Wyatt miniDAWN Treos multi-angle light scattering detector (Wyatt Technology Corp., Santa Barbara, Calif., USA) were used to calculate absolute molecular weight based on do/dc values experimentally determined using offline injections into the RI detector.

2.2.3 Microsphere Fabrication and Drug Loading

Curcumin encapsulated PPS microspheres were prepared using a modification of the oil-in-water (O/W) emulsion solvent evaporation method [26, 29]. Briefly, curcumin (20 mg) and PPS (20 mg) were dissolved in a 10:1 mixture of chloroform (1.5 mL) and methanol (0.15 mL) and ultrasonicated (Cole-Parmer, USA) until both polymer and curcumin were completely dissolved to form the oil (0) phase. The 10% methanol was necessary to achieve curcumin solubility. The 0 phase was then emulsified in 1% (w/v) aqueous PVA solution (6 mL) using an Ultra-Turrax TP 18-10 homogenizer (Janke and Kunkel K G, IKA-WERK) at 20,000 rpm for 1 minute. For solvent removal, the emulsion was then subjected to high vacuum (~635 mm Hg) using a rotary evaporator (Rotavapor RII, BUCHI, Switzerland). Microspheres were then recovered by centrifuging (Allegra X-12 Centrifuge, Beckman Coulter, USA) the remaining aqueous solution at 16,500×g for 5 minutes. The microspheres were then washed once with deionized water and lyophilized (Labconco Freezone 4.5, USA). Unloaded control PPS microspheres were made using the same method described above but without addition of curcumin.

2.2.4 Microsphere Characterization

Curcumin encapsulated microspheres were characterized for size and morphology by scanning electron microscopy (SEM, Hitachi S-4200, Hitachi Ltd, Tokyo, Japan). The microspheres were suspended in a water drop and placed on a double sided carbon tape attached to an aluminum stub, air dried, and then sputter coated with gold for 30 seconds. Curcumin encapsulation was confirmed by fluorescent microscopy using a Nikon Eclipse Ti inverted fluorescence microscope (Nikon Instruments Inc., Melville, N.Y.). To do so, microspheres were suspended into a water drop on a glass slide and imaged after covering with a glass cover slip. Drug loading in the microspheres was determined by fully dissolving microspheres in DMSO (1 mg/mL) overnight, centrifuging at 16,500×g for 3 min, and quantifying the curcumin concentration in the supernatant using fluorescence of curcumin (excitation 488 nm, emission 535 nm) in a plate reader (Tecan Group Ltd., Mannedorf, Switzerland). Drug loading and encapsulation efficiency were calculated from the extracted curcumin using established methods [42]. Size of the microspheres was quantified using ImageJ 1.45s software (Freeware, NIH, Bethseda, Md.) by measuring SEM diameters of >100 microspheres.

2.3 ROS-Dependent Curcumin Release Kinetics In Vitro

In vitro release profiles of curcumin from PPS microspheres were obtained by exposing the PPS microspheres to 0, 0.5, 5, 50, 500, and 882 (3 wt %) mM concentrations of $H2O2$ for 56 days and quantifying the amount of released curcumin by fluorescence (excitation 488 nm, emission 535 nm). PBS (1×, pH 7.4) containing 0.1% w/v N-acetylcysteine (NAC) and 0.01% w/v butylated hydroxytoluene (BHT) was used as the release buffer. Microspheres containing 5 curcumin were suspended in 1 mL release buffers with $H2O2$ and placed in the top of transwell inserts (pore size of 400 nm) in 24-well plates. The wells were sealed with parafilm and incubated at 37° C. under constant shaking (30 rpm). Releasate was collected from the bottom chamber at regular time intervals and the release buffer was removed and replaced with fresh buffer. Removed release buffer was diluted 2× with 100% ethanol for complete dissolution and evaluated by fluorescence on a plate reader (Tecan Group Ltd., Mannedorf, Switzerland) at excitation 488 nm, emission 535 nm based on a curcumin fluorescence standard curve prepared in the same buffer. Control experiments were performed after 14 hours of incubation to ensure no effect of $H2O2$ on quantification of free curcumin (data not shown). All release experiments were performed in triplicate. Release experiments were repeated with 3-morpholinosydnonimine (SIN-1) which generates nitric oxide, superoxide, and peroxynitrite [43, 44]. Release buffers containing 0.1 mM, 1 mM, and 2 mM SIN-1 were prepared. In order to measure on demand delivery of encapsulated curcumin, microspheres placed in the top of transwell inserts were subjected to intermittent SIN-1 for 4 day intervals for a maximum of 72 days. Microspheres were subjected to control buffer for 4 days for the "off" phase, and the respective SIN-1 concentration was added at the beginning of each "on" phase of the experiment. Buffer containing SIN-1 was replaced with control buffer at each subsequent "off" interval.

2.4 In Vitro Curcumin Delivery 2.4.1 Curcumin-Mediated Cell Survival

NIH-3T3 fibroblasts were transduced with lentivirus to express luciferase (LR-3T3s) as described previously [45]. LR-3T3s were cultured in DMEM supplemented with 10% FBS and 1% p-s, then seeded at 5000 cells/well in a black-walled 96-well plate and incubated at 37° C. overnight. The media was replaced with fresh media containing no microspheres, blank PPS microspheres, or PPS microspheres containing curcumin. Varying concentrations of $H2O2$ were added ranging from 0-1 mM. The cells were then incubated at 37° C. for 24 hours. Fresh media containing D-luciferin (Biosynth, Itasca, Ill.) was added to each well at a final concentration of 5 μg/mL, and the luminescence from the viable cells was measured using an IVIS 200 (Xenogen). Luminescence images were analyzed with Living Image® software Version 3.2 (Perkin Elmer).

2.4.2 Cellular Internalization of Microspheres

3T3 fibroblasts and RAW 264.7 macrophages were seeded in 6-well plates (230,000 cells/well for flow cytometry) or an 8-well chamber cover slip (12,000 cells/well for microscopy) in DMEM supplemented with 10% FBS and 1% p-s and allowed to adhere overnight. Cells were then treated with fresh DMEM with curcumin-loaded PPS microspheres at a curcumin dose of 3.4 µM. One cohort of RAW macrophages were activated to a pro-inflammatory M1 phenotype with 100 ng/mL of LPS and 100 U/mL of interferon-gamma (IFN-γ) [46, 47] to assess the effect of macrophage phenotype on microparticle uptake. All groups were incubated with treatments for 24 hours, then cells were washed 3 times with PBS. For confocal microscopy, cells were imaged in phenol-red free DMEM media with 0.05% trypan blue in order to determine intracellular uptake of microspheres by different cell types. For flow cytometry (FACSCalibur, BD Biosciences), cells were harvested in 0.05% trypan blue in PBS prior to measurement of intracellular curcumin fluorescence.

2.4.3 Macrophage Intracellular ROS Production In Vitro

RAW 264.7 cells were seeded at 230,000 cells/well in 6-well plates in DMEM supplemented with 10% FBS and 1% p-s and were allowed to adhere overnight. Cells were then treated for 1 hour with either blank PPS microspheres or curcumin-loaded PPS microspheres in fresh DMEM medium at a curcumin concentration of 3.4 and then 100 ng/mL of LPS and 100 U/mL of IFN-γ was added to the media prior to an additional 24 hours of incubation to stimulate production of ROS. Control groups consisted of cells without LPS/IFN-γ stimulation and stimulated cells with no microparticle treatment. After 24 hours of stimulation, cells were washed with PBS and then incubated with 5 µM H2-DCFDA in phenol red-free, serum-free DMEM for 25 minutes. Cells were washed with PBS and harvested in 0.05% trypan blue in PBS. ROS-induced, intracellular fluorescence was measured via flow cytometry (FACSCalibur, BD Biosciences) and analyzed using FlowJo software. Curcumin fluorescence was compensated for using cells receiving the same treatments but without addition of the DCFDA dye.

2.4.4 ELISA to Measure Effects of Curcumin Microspheres on MCP-1

RAW 264.7 macrophages were seeded at 20,000 cells/well in a 96-well plate in DMEM supplemented with 10% FBS and 1% p-s and were allowed to adhere overnight. Cells were then treated for 1 hour with either blank PPS microspheres or curcumin-loaded PPS microspheres in fresh DMEM medium (phenol red-free, 1% FBS, 1% p-s) at a curcumin concentration of 3.4 and then the media was supplemented with 100 ng/mL of LPS and 100 U/mL of IFN-γ for an additional 2 hours to stimulate production of ROS. Unstimulated cells were used as a control. After incubation with microspheres and LPS/IFN-γ, the treatments were removed and the cells were given fresh, phenol-red free DMEM (1% FBS, 1% p-s). After 24 hours of incubation, culture media was harvested for measurement of monocyte chemoattractant protein-1 (MCP-1) concentration using an ELISA kit (PeproTech). Protein concentration was normalized to relative cell number using a lactate dehydrogenase (LDH) assay (Promega) performed on lysed cells (KDalert lysis buffer, Life Technologies).

2.5 In Vivo 2.5.1 Mouse Hind Limb Ischemia Model

Type 1 diabetes was induced in 8-week-old male FVB mice (Jackson Laboratories) with daily intraperitoneal injections of streptozotocin (50 mg/kg) for 5 consecutive days after a 5 hour fast [48]. Glucose levels were measured immediately before induction of hind limb ischemia, and mice with levels above 300 mg/dl were considered diabetic. After 4 weeks of hyperglycemia, hind limb ischemia [49] was surgically induced as described previously [50]. Briefly, the femoral artery and vein of the right hind limb were ligated with 6-0 silk sutures at two locations: immediately proximal to the origins of the superficial epigastric artery and deep branch of the femoral artery, and proximal to the vessels that branch toward the knee. Major side branches were also ligated, and the ligated segment of the femoral artery and vein was excised. The skin incision was closed with interrupted 5-0 nylon sutures. Surgery was performed under isoflurane anesthesia at normal body temperature. Analgesia (10 mg/kg ketoprofen) was administered subcutaneously pre-operatively and every 18-24 hours post-operatively until animals exhibited normal appearance and behavior. At 4 hours post-surgery, the ischemic hind limb was treated with saline, blank PPS microspheres, or curcumin-loaded PPS microspheres at 5 mg/kg curcumin and 10.3 mg/kg PPS via intramuscular injection into the gastrocnemius and adductor muscles (5×20 µL injections). Mice were fed a standard chow diet ad libitum and had free access to water.

2.5.2 In Vivo Local Retention of Curcumin Delivered from PPS Microspheres

In a separate cohort of mice, hind limb ischemia was induced, and at 4 hours post-surgery, curcumin-loaded microspheres were injected into both the ischemic and control limbs (5 mg/kg curcumin in 10.3 mg/kg PPS) via intramuscular injection. The kinetics of local release of curcumin from PPS microspheres was imaged non-invasively using a Xenogen IVIS 200 to measure curcumin fluorescence (ex: 445-490 nm, em: 515-575 nm).

2.5.3 ROS Measurement in Extracted Gastrocnemius

After 7 days of ischemia, the gastrocnemii of mice from the different treatment groups were extracted immediately postmortem and transferred into PBS in a 24-well plate. A background image of both sides of the gastrocnemius was collected with a Xenogen IVIS 200 (ex: 670 nm, em: 700 nm). The gastrocnemius was then incubated with an ROS-sensitive, fluorescent hydrocyanine dye at a concentration of 100 µM (ROSstar 650, Li-Cor Biosciences, Lincoln, Nebr.) [51] for 45 minutes in the dark then washed with PBS. Both sides of the gastrocnemius were then imaged again with an IVIS 200 (ex: 670 nm, em: 700 nm). ROS was also measured with the hydrocyanine dye method in one untreated animal at day 1 to confirm increased ROS levels in the gastrocnemius at an early time point. The average radiance from the ROS-sensitive fluorescence was quantified for all gastrocnemii images using Living Image® software Version 3.2 (Perkin Elmer).

2.5.4 Intravital Hyperspectral Imaging of Hemoglobin Oxygen Saturation

Hyperspectral imaging of the footpads was performed at days 0, 2, 4, and 6 post-surgery as described previously [39, 50]. Briefly, a halogen lamp coupled into a liquid light guide provided sample illumination, and the collection arm consisted of a variable focal length camera lens (Navitar, f=18-108 mm) and liquid crystal tunable filter (CRi, Inc.) mounted on a cooled CCD camera (Andor, 1392×1040 pixel). Diffuse reflectance images were collected from 500-620 nm in 8-nm increments and calibrated with measurements of the dark offset and reflectance from a diffuse reflectance standard (Spectralon). Hemoglobin oxygen saturation was then calculated from a modified version of Beer's law that solves for the hemoglobin saturation in each pixel using linear least-squares regression [39, 52-54]. Average hemoglobin saturation values were computed for each footpad by averaging all pixels, and the ischemic footpad measurement was normalized to that of the contralateral footpad.

2.5.5 Perfusion Imaging

Perfusion images of the footpads were acquired at days 0, 2, and 7 post-surgery with a commercial laser speckle perfusion imager (Perimed). An average perfusion value was computed for each footpad, and the ischemic footpad perfusion was normalized to that of the contralateral footpad.

2.5.6 Intravital Imaging of Vascular Morphology with Optical Coherence Tomography At day 7 post-surgery, images of the hind limb vasculature were collected through the skin non-invasively using a swept-source optical coherence tomography (OCT) system with a 1060 nm, 100 kHz source (Axsun Technologies, Inc.) [50, 55]. Speckle variance OCT volumes [56] were collected in a 4 mm×4 mm area covering the gastrocnemius muscle region to monitor remodeling of vessels in response to hind limb ischemia [39]. The speckle variance B-scans were processed as described previously [50, 55], and an average intensity projection over ~1.5 mm in depth was computed to visualize all vessels within the volume in a 2D image. The projection images of the vasculature were filtered to enhance contrast and connectivity [50, 55, 57], and the distribution of vessel diameters in each image was quantified.

2.5.7 Histological Evaluation of Host Response to Microspheres

At 7 days post-surgery, the mice were sacrificed and the gastrocnemii were removed, fixed with 10% formalin for 24 hours, and embedded in paraffin. Histological sections (4 μm) were cut and stained with hematoxylin and eosin (H&E) in order to assess the host response to the microsphere injections.

2.6 Statistical Analysis

All data are reported as mean+standard error of the mean (SEM). Analysis of Variance (ANOVA) with a post-hoc Tukey test for multiple comparisons was used to determine treatment effects and $p<0.05$ was considered significant. For in vivo hemoglobin oxygen saturation and perfusion endpoints, an ANOVA general linear model analysis with a post-hoc Tukey test for multiple comparisons was performed to determine the treatment effect over the full time course. For comparisons between groups within individual time points, a Wilcoxon Rank Sum test was performed.

3. Results

3.1 Microsphere Synthesis and Characterization

3.1.1 Synthesis and Characterization of PPS

PPS was synthesized by ring opening polymerization of propylene sulfide using ECT as initiator and TPPCl as catalyst at 60° C. through thioacyl group transfer (TAGT) polymerization. The molecular weight and polydispersity of PPS as determined by GPC were $M_n$=17,700 g/mol and PDI=1.36, respectively. The polymer structure was confirmed by $^1$H NMR spectra recorded in $CDCl_3$: 1.25-1.45 (s, $CH_3$), 2.5-2.7 (m, CH), 2.85-3.0 (m, —$CH_2$).

3.1.2 Microsphere Characterization

Curcumin-loaded microspheres were characterized for size and morphology by SEM (FIG. 1). Measurements from SEM images indicated that the microspheres had an average diameter of 1.33±0.55 μm (mean±SD, n>100). Curcumin encapsulation was qualitatively confirmed by fluorescent microscopy. Drug loading and encapsulation efficiency were 49% w/w curcumin/PPS and 40%, respectively, as determined by extraction of the drug from the microspheres using DMSO.

3.2 Curcumin ROS-Dependent Release Kinetics

Figures 2A, 2B:
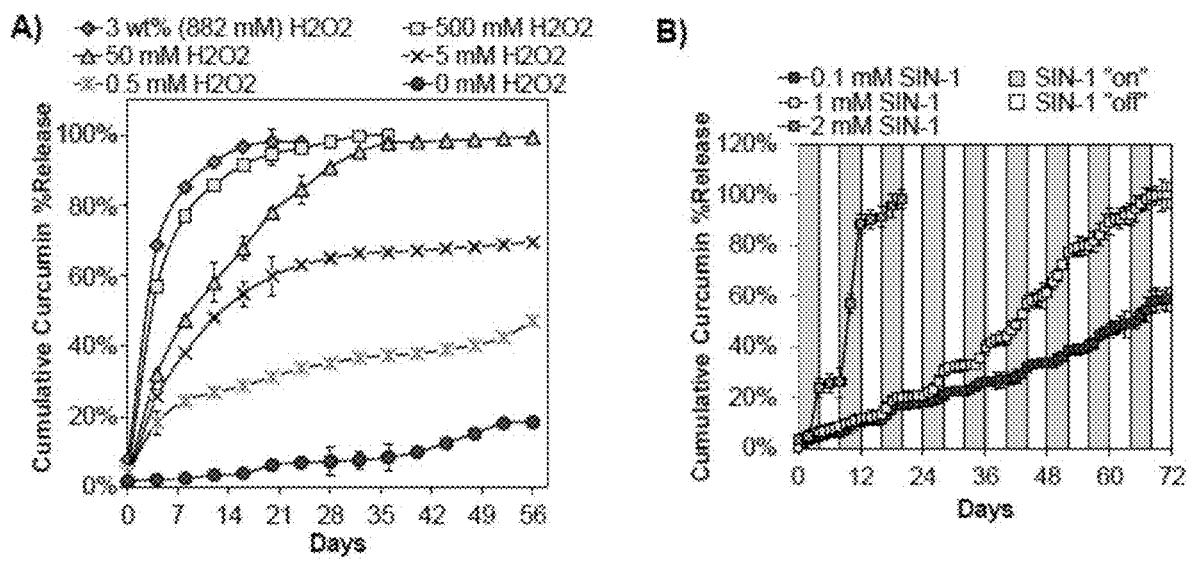
FIGS. 2A-2B: Curcumin release from PPS microparticles was ROS dose-dependent and on demand.

For in vitro release kinetics experiments (FIG. 2A), the rate of curcumin release was dependent on the concentration of H2O2. There was little release in the absence of H2O2, and only approximately 20% of the curcumin was released over the entire 56-day period in PBS. For other conditions, the rate of release of curcumin correlated to the dose of $H_2O_2$.

On demand release of curcumin was exhibited by PPS microspheres intermittently exposed to SIN-1 which rapidly degrades (half-life of 1-2 hours [58]) to simultaneously produce nitric oxide and superoxide. These free radicals combine to form the oxidant peroxynitrite [43]. The samples were exposed to SIN-1 off/on cycles for 4 day intervals for a maximum duration of 72 days to assess whether on demand release could be achieved over an extended timeframe. When microspheres were incubated in a range of SIN-1 concentrations, including 1 mM which has been used to mimic oxidative stress conditions in vitro [34, 44, 59], a concentration-dependent and on demand release profile was observed (FIG. 2B, green bars=+SIN-1, white bars=no SIN-1). The slope of the release curve was higher during the SIN-1 "on" phases than the "off" phases for all doses tested. Together, the H2O2 and SIN-1 release experiments demonstrate ROS concentration-dependent, on demand release of the antioxidant curcumin from PPS microspheres.

3.3 In Vitro Curcumin Delivery

3.3.1 Curcumin-PPS Microspheres Enhance Cell Survival In Vitro

Figures 3A, 3B:
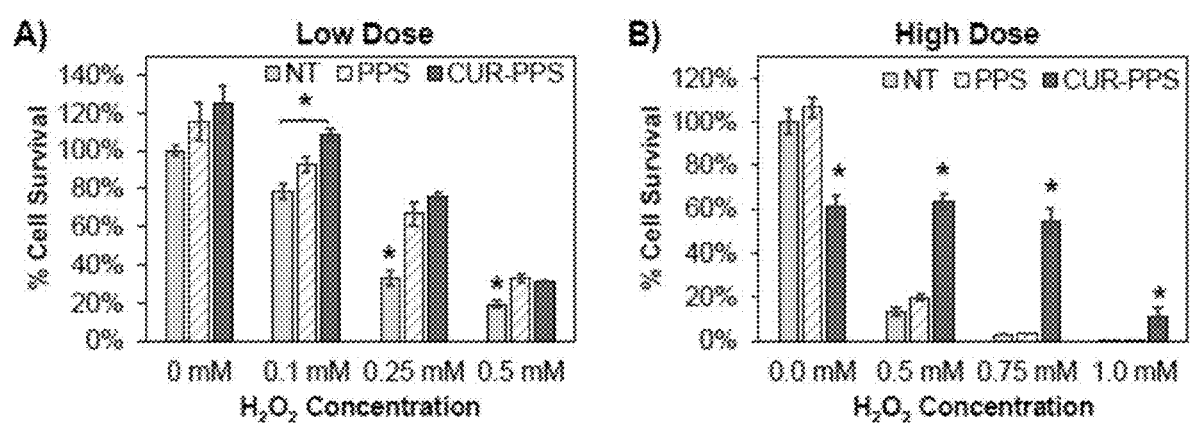
FIGS. 3A-3B: Curcumin loaded PPS microparticles reduce the cytotoxicity of $H_2O_2$. Cell survival was measured for luciferase expressing 3T3 fibroblasts incubated for 24 hours with blank PPS microspheres, curcumin-PPS microspheres, or vehicle in media containing varied doses of $H_2O_2$. Curcumin dose is 3.4 μM in (FIG. 3A) and 27.1 μM in (FIG. 3B). Blank PPS microparticles represent the equivalent polymer dose (2.5 μg/mL PPS in (FIG. 3A) and 20.4 μg/mL PPS in (FIG. 3B)) used to deliver the corresponding curcumin dose. *p<0.05 relative to other treatment groups within each $H_2O_2$ dose. n=3 per group.

Next, the ability of curcumin-PPS microspheres to salvage cell viability under cytotoxic levels of ROS was assessed. For a low dose of curcumin-PPS (3.4 μM curcumin, 2.5 μg/mL PPS), it was found that microspheres were cytocompatible and showed a significant therapeutic benefit up to 0.5 mM H2O2 ($p<0.05$) (FIG. 3A). At this level of ROS, both blank PPS and curcumin-PPS showed a protective effect since PPS itself scavenges H2O2 (FIG. 3A) [32]. A higher dose of curcumin-PPS (27.1 μM curcumin, 20.4 μg/mL PPS) was then tested (FIG. 3B). Although approximately 40% baseline toxicity was seen in the curcumin-PPS treated cells in the absence of H2O2, there was a greater therapeutic effect with curcumin-PPS under higher levels of ROS (up to 1 mM $H_2O_2$). Blank PPS microspheres did not rescue cell viability under these higher H2O2 concentrations. Together, these data indicate that both blank PPS and curcumin-PPS microspheres improve cell viability under oxidative stress conditions in a dose-dependent manner. Under greater oxidative stress levels, curcumin-PPS is superior to PPS alone. The lower dose of microspheres was sufficient to improve cell survival in 0.5 mM H2O2 conditions without baseline cytotoxic effects, so this microsphere dose was selected for use in further in vitro experiments.

Figure 4A:
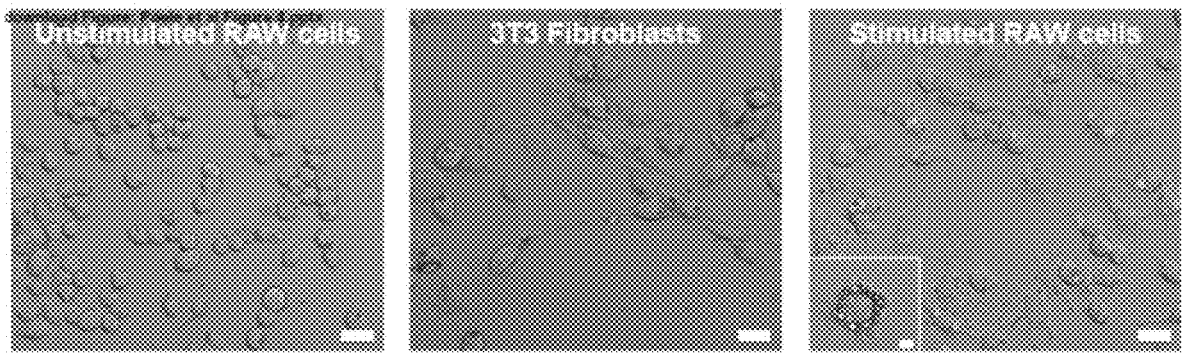
FIGS. 4A-4D: Curcumin-PPS microspheres are preferentially internalized by activated macrophages and exert functional effects on ROS generation and MCP-1 secretion.
Figure 4B:
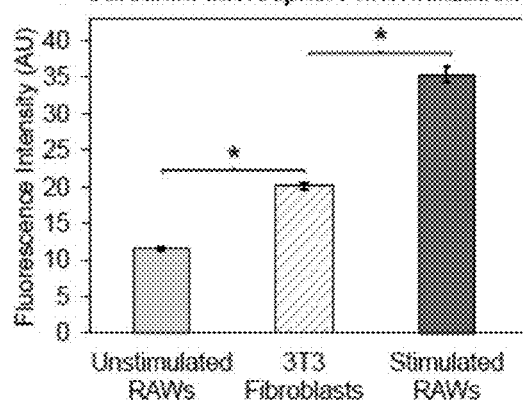

3.3.2 Microspheres are Preferentially Internalized by LPS/IFN-☐-Activated Macrophages In order to test whether the microparticles may preferentially target activated, phagocytic cells in vivo based on their physical characteristics, in vitro cellular internalization of curcumin-loaded PPS microspheres was assessed in 3T3 fibroblasts, RAW cells at baseline, and RAW cells activated to a pro-inflammatory M1 phenotype through a combination of LPS and IFN-[46, 47]. After 24 hours of treatment, confocal microscopy and flow cytometry qualitatively and quantitatively indicated that stimulated RAWs internalized the microspheres at a significantly higher rate than control cell types (FIG. 4A-B). Confocal microscopy z-stacks confirmed that microspheres were internalized rather than adsorbed to the outside of the cell membrane (FIG. 4A). Quantification of curcumin-PPS microsphere uptake with flow cytometry confirmed that curcumin-PPS microspheres were preferentially internalized by pro-inflammatory M1 macrophages (FIG. 4B).

3.3.3 Curcumin PPS Reduces Intracellular ROS Levels In Vitro

Figure 4C:
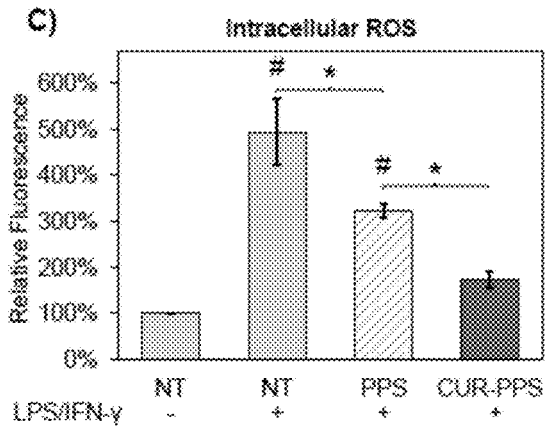

Curcumin-PPS microspheres exerted a functional effect on intracellular ROS levels in RAW cells activated by LPS and IFN-γ. Flow cytometry quantification of intracellular ROS showed that activated RAWs treated with either blank PPS microspheres or curcumin-loaded PPS microspheres had significantly lower levels of ROS than untreated, activated RAWs ($p<0.05$) (FIG. 4C). Additionally, ROS levels in activated RAWs treated with curcumin-PPS microspheres were approximately 50% lower than in blank PPS-treated cells ($p<0.05$) and statistically equivalent to ROS levels in non-activated RAW cells ($p>0.05$).

3.3.4 Secretion of Chemokine MCP-1 is Reduced by Curcumin-PPS In Vitro

Figure 4D:
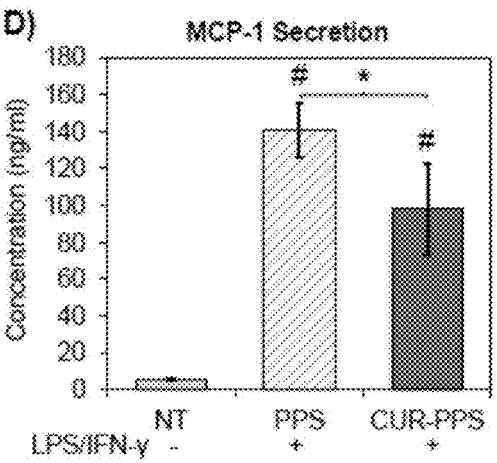

After characterizing the antioxidant activity of both unloaded and curcumin-loaded PPS microspheres, we sought to confirm that curcumin loading provides additive anti-inflammatory activity relative to blank PPS microspheres through suppression of the NF-κB pathway [18, 19]. To do so, we compared the effect of curcumin-loaded PPS microspheres to that of blank PPS microspheres on secretion of MCP-1, an inflammatory chemokine whose expression is mediated by NF-κB activity [60, 61], in activated macrophages. Curcumin-loaded microspheres significantly reduced MCP-1 secretion in activated macrophages in comparison to blank PPS-microspheres ($p<0.05$) (FIG. 4D).

3.4 Response to Curcumin-PPS In Vivo

Figures 5A, 5B, 5C:
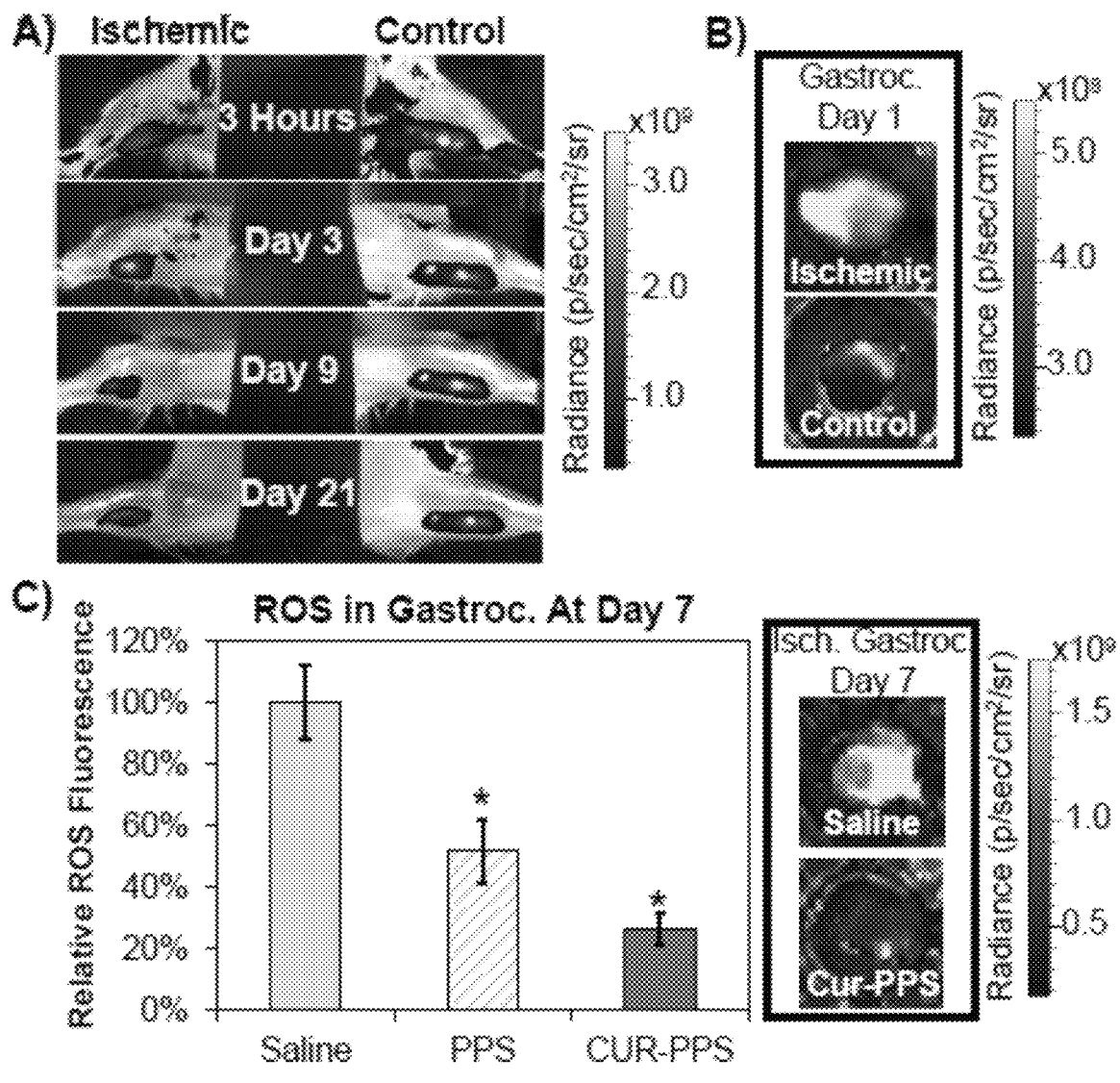
FIGS. 5A-5C: PPS microspheres provide sustained, on demand local curcumin release and reduce tissue ROS levels in the ischemic limb in vivo.

3.4.1 Curcumin PPS Microspheres are Retained Locally and Reduce ROS Levels in the Ischemic Hind Limb Muscle Local retention of curcumin-PPS microspheres in the hind limb muscle was assessed using an IVIS system to non-invasively image curcumin fluorescence over time after induction of hind limb ischemia (n=5 mice, representative time course in FIG. 5A). In the ischemic limb, curcumin was released more rapidly than in the control limb, presumably due to the increased level of ROS present during ischemia. ROS levels are increased in an untreated ischemic muscle as early as 1 day post-surgery as indicated by a greater than 2-fold increase in fluorescence of the ROS-sensitive hydrocyanine dye relative to the control muscle (FIG. 5B). During the 3 week period following surgery, the average curcumin fluorescence signal in the control limb remained ~4.8× greater than tissue background fluorescence, while the average ischemic limb signal decreased from 6.4× to 3.2× greater than background fluorescence by day 3 post-injection then leveled off to 2.6× from day 3 to day 21 as the limb recovered from hypoxia.

After 7 days of ischemia, the levels of ROS-sensitive fluorescence in the extracted gastrocnemius muscles were significantly lower for mice receiving treatment with either blank or curcumin-loaded PPS microspheres relative to the saline-treated group ($p<0.05$) (FIG. 5C). Additionally, there was a statistically insignificant trend ($p=0.07$) for decreased ROS with curcumin-PPS treatment relative to blank-PPS treatment.

Figures 6A, 6B:
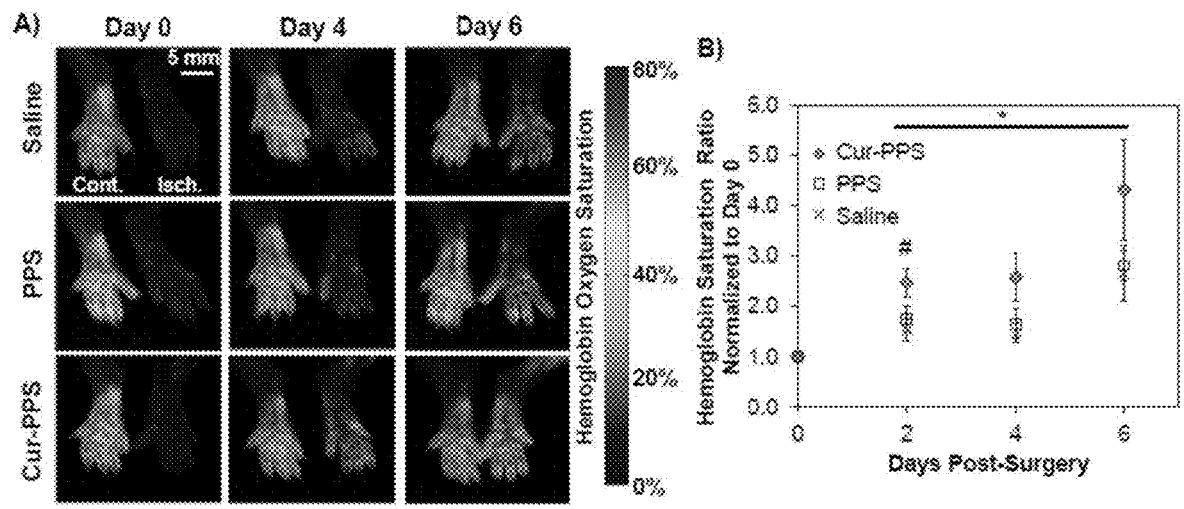
FIGS. 6A-6B: Curcumin-loaded PPS microspheres improved ischemic limb recovery in the setting of diabetes in vivo.

3.4.2 Enhanced Recovery of Blood Oxygenation and Perfusion in the Ischemic Limb Functional recovery from ischemia was evaluated over a one week period in order to assess the therapeutic effect of curcumin-PPS during a time frame in which ROS overproduction in the ischemic limb is known to occur [15, 62]. Hemoglobin oxygen saturation measured non-invasively with hyperspectral imaging (representative images FIG. 6A) is significantly increased in the curcumin-PPS treated group relative to the blank PPS and saline-treated groups over the time course of ischemic recovery (days 2, 4 and 6 combined, $p<0.05$) (FIG. 6B). At day 2, the curcumin-PPS group has a significantly higher hemoglobin saturation ratio compared to the saline group, while the PPS and saline groups are not significantly different across the time course ($p>0.9$) (FIG. 6B). Similarly, perfusion imaging of the footpads indicated that curcumin-PPS microsphere treatment significantly increases recovery of distal blood flow over the time course of one week relative to blank PPS treatment (days 2 and 7 combined, $p<0.05$). At day 2, the curcumin-PPS group has a significantly greater perfusion ratio than the saline and blank PPS groups.

Figures 7A, 7B:
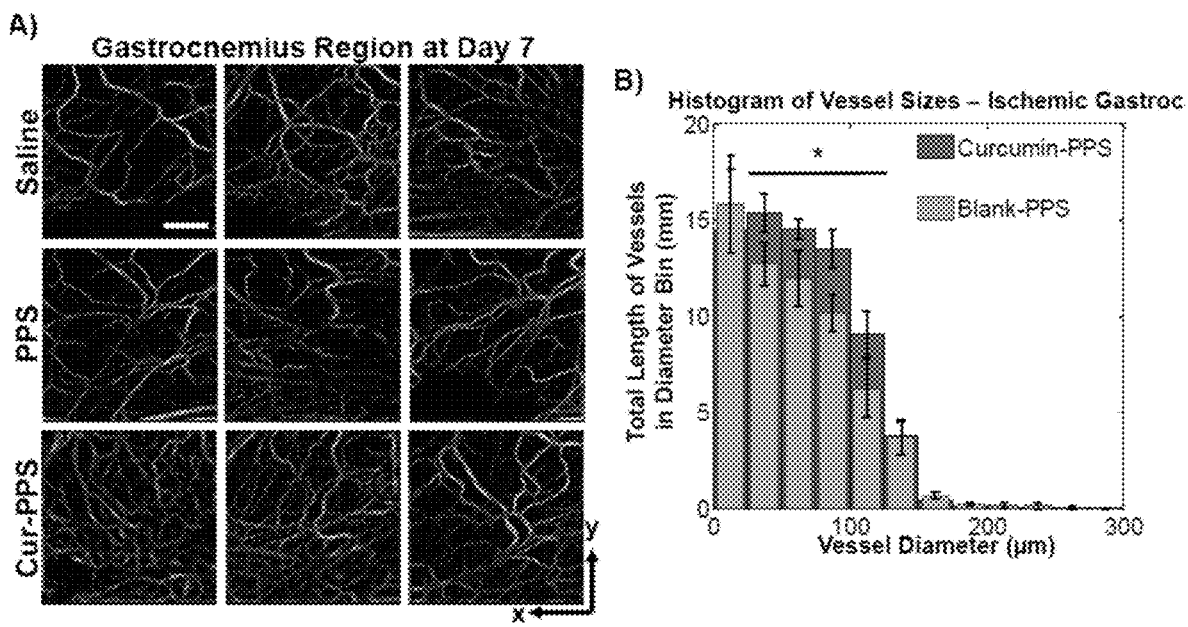
FIGS. 7A-7B: Vessel morphology was imaged non-invasively on day 7 with speckle variance OCT (n=4-5/group).
Figure 8:
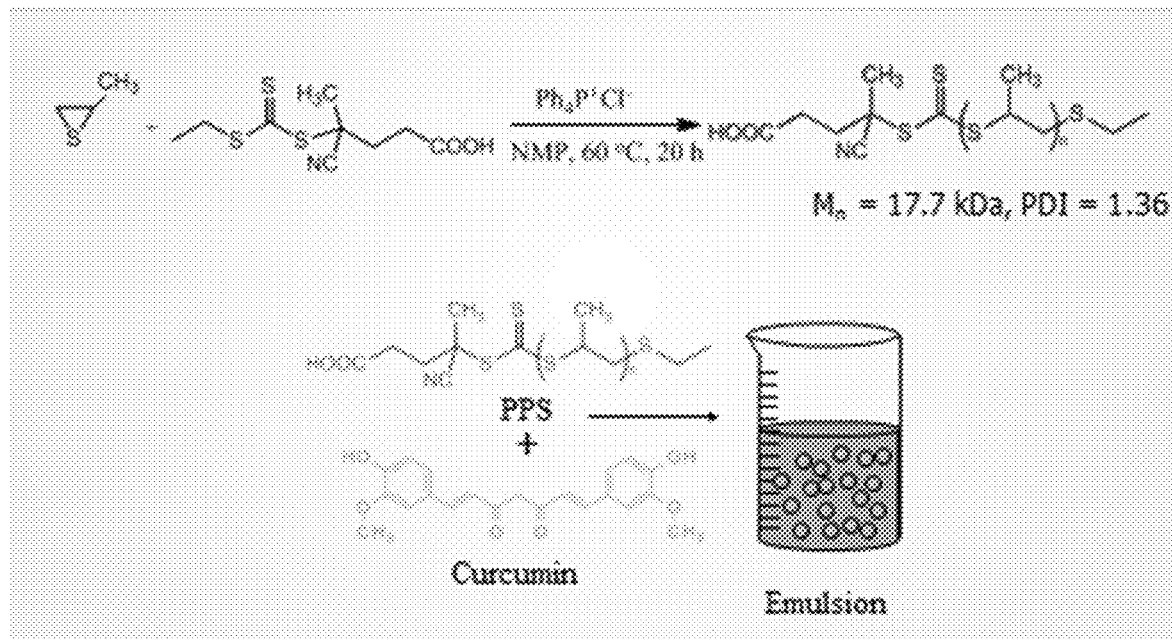
FIG. 8 illustrates a method of preparing an emulsion of the present invention.
Figure 9:
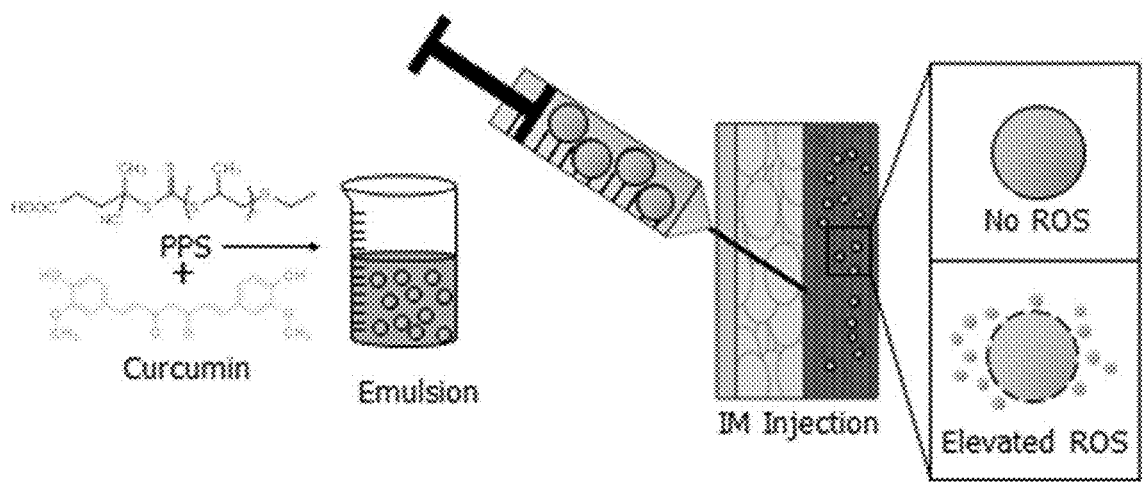
FIG. 9 illustrates a method of preparing and using an emulsion of the present invention.

3.4.3 Intravital Imaging of Vascular Morphology in the Ischemic Gastrocnemius The effect of microsphere treatments on vessel remodeling in the ischemic hind limb was imaged non-invasively using speckle variance OCT [39, 50, 56]. Representative images in FIG. 7A provide visualization of vessel morphology in the gastrocnemius muscle at day 7 post-surgery, and the diameter distribution for the curcumin-PPS treated mice showed a significant increase in the length of vasculature with diameters between 25 μm and 125 μm relative to the blank PPS microsphere group ($p<0.05$) (FIG. 7B).

3.4.4 Microspheres are Histocompatible in the Ischemic Limb

H&E staining showed that the muscle status was heterogeneous across cross-sections of the ischemic limb gastrocnemius for all treatment groups at day 7 following induction of ischemia. The majority of the muscle fibers within the gastrocnemius appeared healthy, but there were interspersed regions showing significant mononuclear cell infiltration associated with fibrous tissue and apparent muscle fiber necrosis. These observations suggest that some negative tissue response to ischemia and/or tissue damage due to syringe insertion into the muscle was present for all groups but that there was no apparent, deleterious host response to the microsphere treatments.

4. Discussion of Example 1

Therapies that target oxidative stress and inflammation in ischemic tissue environments have potential to improve the impaired neovascularization associated with diabetes [15, 16]. Curcumin is a promising candidate due to its demonstrated safety in humans and its combined anti-inflammatory and antioxidant properties; however, curcumin bioavailability is limited by low serum and tissue levels (irrespective of administration route), rapid metabolism, and systemic elimination [18, 20, 23]. For local delivery applications, delivery vehicles are needed that can overcome the limitations of bioavailability due to the extreme hydrophobicity and instability of free curcumin under neutral-basic pH conditions [63, 64]. Previous approaches to improving curcumin bioavailability in vivo have included exosomes [25] and liposomes [22] for systemic administration, and stimuli-responsive nanoparticles for local injections at sites of inflammation [4]. However, micron-sized particles may be better suited for forming a stable depot for sustained, localized delivery to an ischemic tissue site. In comparison to nanoparticles, microparticles have reduced systemic absorption and are less apt to diffuse away from the injection site, thus providing sustained, local drug release over a longer time frame [65]. Additionally, particles from 0.5 to 5 μm in diameter could be used to selectively target uptake by phagocytic cell types [66-68], as we have shown in vitro in activated macrophages for our particles with an average diameter of 1.3 μm (FIG. 4A-B). Microparticles composed of PLGA have been used to encapsulate curcumin for sustained release as a cancer therapeutic [26]. However, the release kinetics can be affected by PLGA autocatalytic degradation, and the degradation products of PLGA cause a local acidification and inflammatory response [27, 28]. To accomplish the goals of providing sustained, local, on demand antioxidant and anti-inflammatory therapy to ischemic tissues under oxidative stress, we have pursued ROS-sensitive PPS microspheres as a delivery vehicle.

PPS was selected as the vehicle for curcumin in this application because its hydrophobicity allows for efficient encapsulation of hydrophobic curcumin via O/W emulsion, and the cargo is released in a bioresponsive, ROS-dependent manner as shown by exposure of the curcumin-loaded microspheres to H2O2 and SIN-1 in vitro (FIG. 2). While a bolus delivery of ROS was used for these cell free experiments in contrast to the continuous ROS generation that occurs in inflamed tissues in vivo, the ranges of H2O2 and SIN-1 doses were selected to include physiologically-relevant ROS concentrations [34] as well as higher doses that demonstrate the ROS concentration-dependency of curcumin release. Though it is difficult to precisely mimic the complex milieu of ROS present in vivo, the dose range of peroxynitrite-generating SIN-1 tested in this work corresponds with doses of up to 1 mM SIN-1 that have been used to mimic pathological conditions on cells [44, 59]. While some of the doses of H2O2 and SIN-1 used in these drug release studies may be superphysiologic, these results demonstrate that the microspheres respond to multiple sources of ROS which contribute to oxidative stress in inflamed tissues. With regards to the PPS microsphere drug-release mechanism, the hydrophobic sulfide is converted to more hydrophilic sulfoxide/sulfone by ROS-mediated oxidation [30]. We expect that this phase change causes swelling and then gradual disassembly of the PPS microparticle matrix into water soluble, unimeric polymers and that progression of this process triggers release of the microsphere cargo. Unlike PLGA, the byproducts of PPS microsphere degradation do not acidify the local environment [27], and PPS has been safely used as a component in nanoparticle and polymersome drug carriers in vitro and in vivo [31, 34, 69].

In addition to its cytocompatibility and utility for drug loading, PPS has inherent therapeutic properties as a H2O2 scavenger [32]. To our knowledge, our group was the first to demonstrate the cell-protective effects of PPS in the presence of cytotoxic levels of ROS in recent work with PPS-containing hydrogels [35]. We have also observed this benefit here with our PPS microparticle-based injectable drug depot as shown in experiments with 3T3 fibroblasts (FIG. 3). Importantly, curcumin was synergistic with PPS, and the curcumin-loaded microparticles showed superior therapeutic benefit compared to blank particles under higher $H_2O_2$ concentrations. In this context, it is presumed that curcumin microparticles injected into tissue would remain within the tissue stroma and release therapeutic curcumin and/or scavenge extracellular ROS to reduce oxidative stress on surrounding skeletal muscle and other resident cells. However, it was also found that fabrication into micron-sized particles enabled preferential curcumin-PPS microsphere uptake by more phagocytic, activated macrophages (FIG. 4A-B), as these particles fall within the size range that is not efficiently internalized by non-phagocytic cell types [66-68]. This preferential targeting to inflammatory cells is desirable since these cells are the primary producers of damaging ROS and pro-inflammatory signals [1, 3, 5]. Furthermore, ROS may also be produced and accumulate in intracellular compartments such as phagosomes and endosomes/lysosomes [70], and targeting antioxidant enzymes to endocytic vesicles may be an effective approach for quenching endosomal superoxide [71]. Thus, tuning of PPS microparticle size to be optimized for phagocyte internalization may enable direct targeting to ROS at their subcellular source. In the current study, blank and curcumin-loaded PPS microspheres significantly reduced intracellular ROS levels in activated macrophages (FIG. 4C). PPS microsphere-mediated ROS scavenging in living cells is a novel finding for PPS, to our knowledge, and the synergy with curcumin is in agreement with previous studies demonstrating the antioxidant effects of curcumin in vitro [4, 72]. Thus, these data suggest that curcumin-loaded PPS microparticles would potentially have a combined mechanism in vivo where curcumin would be released extracellularly and also intracellularly primarily within activated, phagocytic macrophages. Curcumin-PPS microspheres also reduced secretion of chemokine MCP-1 in activated macrophages (FIG. 4D), confirming anti-inflammatory activity through inhibition of the NF-κB pathway [60].

Diabetes-induced oxidative stress impairs post-ischemic neovascularization, and reduction of ROS represents a promising approach to remedy PAD [15, 16]. Curcumin is a promising candidate in this context, and it has been shown to have therapeutic benefit in preclinical models of inflammation and ischemia/reperfusion injury using delivery approaches such as systemic injection of free curcumin [21], systemic injection of exosomes [25] and liposomes [22], and local injection of stimuli-responsive nanoparticles [4]. However, sustained, ROS-demanded delivery of curcumin from a local depot has yet to be investigated in a model in which ischemia and ROS production are exacerbated by diabetes. In the current work, we have shown that in vitro rate of release of curcumin from PPS microparticles is modulated by environmental levels of ROS such as H2O2 and peroxynitrite over a sustained time frame (FIG. 2). This on demand delivery mechanism was also demonstrated in vivo. Increased ROS in the ischemic hind limb mediated rapid release of curcumin from PPS microspheres (FIG. 5A-B), while in the normoxic control limb, microspheres were retained at the site of injection without significant drug release over the 21-day time frame tested. The stable curcumin fluorescence signal observed in the control limb over time suggests that the microsphere depot remained intact in the absence of pathological levels of ROS. This on demand release mechanism was also found to have significant ROS scavenging effects in vivo, and the curcumin-PPS microspheres significantly reduced ROS in the ischemic muscle 7 days following delivery. In this study, the blank PPS microspheres again showed an intermediate reduction of local ROS (FIG. 5C). These in vivo therapeutic studies focused on the acute phase of recovery since the control animals in this model also showed functional improvements at later time points (FIG. 6B). Based on pilot studies in which free curcumin formed crystals in vitro and exacerbated ROS levels in ischemic tissue, we did not pursue free curcumin treatments in this work.

The functional effects on vascular recovery in the diabetic mouse hind limb ischemia model were investigated with non-invasive optical imaging techniques [39, 50]. Hyperspectral imaging of hemoglobin oxygen saturation (FIG. 6), perfusion imaging of the footpads, and OCT of vessel morphology in the gastrocnemius (FIG. 7) revealed that the curcumin-PPS microspheres significantly improved recovery in this model of diabetic PAD. Controlled, on demand release of PPS and curcumin may help keep local levels of ROS within an optimal range, since both too much [15, 16, 73] and too little ROS [62, 74] are detrimental to angiogenesis and ischemic recovery. The greater functional benefit observed from curcumin-PPS microspheres relative to blank PPS particles in this study may be due to the more pleiotropic effects of curcumin in addition to scavenging ROS, including inhibition of NF-κB activity, reduction of proteolytic enzyme levels, inhibition of platelet aggregation, and other anti-inflammatory, antioxidant, and antidiabetogenic effects [18]. Overall, these results are promising for the context of excessive ROS and inflammation in diabetes, and there is an opportunity to optimize dosing and pharmacokinetics in vivo to achieve maximal therapeutic benefit.

Example 2

This example demonstrates an embodiment of the present invention, specifically, a reactive oxygen species (ROS)-sensitive microsphere system consisting of poly(propylene sulfide) (PPS) and superoxide dismutase mimetic 4-hydroxy-TEMPO benzoate was synthesized through oil-in-water emulsion, and the ability to target multiple ROS in an environmentally-responsive manner was evaluated. The hydrogen peroxide ($H_2O_2$) and peroxynitrite-scavenging activity of PPS and the superoxide-scavenging activity of tempo benzoate were confirmed in vitro using cell-free, ROS-producing systems. A mouse model of diabetic peripheral arterial disease (PAD) with a significant therapeutic window for reducing oxidative stress and improving the vascular response to hind limb ischemia was identified for use in evaluating the effects of the tempo-PPS microspheres in vivo. A high dose of either blank PPS or tempo-PPS microspheres was shown to significantly scavenge $H_2O_2$ in the ischemic muscle. Functionally, a low dose of either blank PPS microspheres or tempo-PPS microspheres improved recovery from hind limb ischemia as measured by hemoglobin saturation and perfusion in the footpads and vessel morphology in the proximal limb using non-invasive imaging techniques. These results suggest that targeting $H_2O_2$ and peroxynitrite in this model with a local depot of PPS is an effective strategy for improving the impaired vascular response associated with chronic hyperglycemia. Overall, this work validates the use of the PPS microsphere system as a promising therapeutic treatment for diabetic PAD and other pathologies with localized oxidative stress.

3. Materials and Methods 3.1 Materials

All chemicals were purchased from Sigma-Aldrich (St. Louis, Mo., USA) except the following. Propylene sulfide (>96%) was purchased from Acros Organics through Fisher Scientific (Pittsburgh, Pa., USA) and was purified by distillation just before polymerization. Dihydroethidium (DHE) and Amplex Red Hydrogen Peroxide/Peroxidase Assay kit were purchased from Thermo Fisher Scientific (Molecular Probes, Waltham, Mass., USA). Peroxynitrite was purchased as a solution in 0.3 M sodium hydroxide from Cayman Chemical (Ann Arbor, Mich., USA).

3.2 Microsphere Synthesis 3.2.1 Synthesis of Poly(Propylene Sulfide) (PPS)

Poly(propylene sulfide) (PPS) was prepared as previously described by anionic polymerization of propylene sulfide using DBU/1-butane thiol as an initiator. Briefly, in a dried and nitrogen flushed 50 mL RB flask, 1,8-diazabicyclo[5.4.0]undec-7-ene (DBU) (4.5 mmol, 0.673 mL) in dry tetrahydrofuran (THF) (25 mL) was degassed for 30 minutes, and the reaction mixture temperature was lowered to 0° C. To this flask, a 30 minute degassed solution of 1-butane thiol (1.5 mmol, 0.161 mL) in THF (20 mL) was added drop wise and allowed to react for 30 minutes. Later, freshly distilled and degassed propylene sulfide (120 mmol, 9.39 mL) monomer was added to the reaction mixture, and the temperature was maintained at 0° C. for 2 h. The reaction was quenched by addition of 2-iodoethanol (2 mmol, 0.40 g) and stirred overnight at RT. The next day, the polymer solution was filtered to remove precipitated salt and further purified by three precipitations into cold methanol before vacuum-drying to yield a colorless viscous polymer.

3.2.2 Characterization of PPS

PPS was characterized for structure, molecular weight, and polydispersity as described previously. The number average molecular weight ($M_n$) and polydispersity (PDI) of PPS were assessed by gel permeation chromatography (GPC, Agilent Technologies, Santa Clara, Calif., USA) using dimethylformamide (DMF)+0.1 M lithium bromide mobile phase at 60° C. through three serial Tosoh Biosciences TSKGel Alpha columns (Tokyo, Japan). An Agilent refractive index (RI) and Wyatt miniDAWN TREOS light scattering (LS) detector (Wyatt Technology Corp., Santa Barabara, Calif., USA) were used to calculate absolute molecular weight based on do/dc values experimentally determined through offline injections into the RI detector. The chemical structure of the PPS was analyzed by $^1H$ nuclear magnetic resonance spectroscopy (NMR) recorded in $CDCl_3$ with a Bruker 400 MHz spectrometer. $^1H$ NMR (400 MHz; $CDCl_3$, δ): =1.3-1.4 (s, $CH_3$), 2.5-2.8 (s, —CH), 2.8-3.1 (s, $CH_2$), 3.72 (t, $CH_2$—OH).

3.2.3 Microsphere Fabrication and Drug Loading

PPS microspheres encapsulating tempo-benzoate ("tempo-PPS" microspheres) were prepared using a modification of the oil-in-water (O/W) emulsion solvent evaporation method as described previously. Briefly, tempo-benzoate (5 mg) and PPS (60 mg) were dissolved in chloroform (1 mL) and ultrasonicated (Cole-Parmer, USA) until both PPS and tempo-benzoate were completely dissolved to form the oil (0) phase. The 0 phase was then added drop-wise in 1% (w/v) aqueous poly(vinyl alcohol) (PVA) solution (7 ml) and emulsified using an Ultra-Turrax TP 18-10 homogenizer (Janke and Kunkel K G, IKA-WERK) at 20,000 rpm for 1 minute. The emulsion was transferred to a round-bottom flask and subjected to high vacuum (~635 mm Hg) using a rotary evaporator (Rotavapor RII, BUCHI, Switzerland) for one hour to remove the chloroform. Microspheres were then recovered by centrifuging the remaining aqueous solution at 7500×g for 8 minutes. The microspheres were then washed once with deionized water to remove excess PVA. To remove free tempo-benzoate crystals, the microspheres were filtered using a Buchner flask and funnel with a fritted disk (10-15 µm porosity) (Sigma-Aldrich, St. Louis, Mo., USA). Lastly, the microspheres were lyophilized (Labconco Freezone 4.5, USA) prior to storage. Unloaded blank PPS microspheres were made using the same protocol without the addition of tempo-benzoate. This method produces microspheres with an average diameter of ~1.3 µm.

3.2.4 Microsphere Characterization

Tempo-benzoate incorporation efficiency in the microspheres was determined using high performance liquid chromatography (HPLC). Lyophilized microspheres were dissolved in HPLC grade acetonitrile (with the aid of heating and ultrasonication) and the solution was filtered. Tempo-benzoate concentration was measured using a Luna® 5 µm C18(2) 100 Å, 250×4.6 mm semi-prep column (Phenomenex, Torrance, Calif., USA) under a linear gradient from 90% water (0.05% formic acid), 10% acetonitrile to 5% water (0.05% formic acid), 95% acetonitrile over 30 minutes. Absorbance of tempo-benzoate was measured at 425 nm after establishing that there was no absorbance interference from a filtered blank PPS sample under the same conditions. Drug incorporation efficiency was expressed as drug content (mass of tempo-benzoate/mass of microspheres) and drug encapsulation efficiency ((actual tempo-benzoate mass/microspheres mass)/(input tempo-benzoate mass/total mass of PPS and tempo-benzoate)).

3.3 ROS Scavenging Activity of Microspheres In Vitro

3.3.1 Superoxide Scavenging In Vitro

In vitro superoxide scavenging activity of the tempo-PPS microspheres was evaluated using a dihydroethidium (DHE) fluorescence assay. DHE has been widely used to detect superoxide, which reacts with DHE to form a specific fluorescent product, 2-OH-ethidium (2OH-E). The effects of PPS and tempo-benzoate on superoxide were determined using a superoxide-generating, cell-free enzymatic system containing 0.046 U/ml xanthine oxidase and 0.2 mM xanthine. Xanthine was prepared in PBS−/− as a stock solution (1.21 mg/mL), and the appropriate volume of xanthine stock solution was added to the xanthine oxidase solution to reach the required final concentration. The xanthine/xanthine oxidase solution (100 μL) was added to wells in a black-walled, 96-well plate containing the following treatments: PBS, blank PPS microspheres (55 μg/mL), free tempo-benzoate (dissolved in acetonitrile then diluted to 5% acetonitrile, 55 μg/mL tempo-benzoate), and tempo-PPS microspheres (55 μg/mL microsphere concentration). Each well contained 10 μL of a treatment. 20 uM DHE from dimethylsulfoxide (DMSO) stock solution was freshly prepared in PBS with a final DMSO content of 0.2%. After 10 minutes, 100 μL of the DHE solution was added to each well (10 uM final DHE concentration) and the fluorescence intensity was measured in a plate reader (Tecan Group Ltd., Mannedorf, Switzerland) over a time frame of 1 hour with an excitation of 405 nm and an emission of 570 nm. These excitation/emission wavelengths were selected in order to improve the specificity of the assay for measuring the superoxide-specific product of DHE oxidation. Specificity of the assay for superoxide detection was confirmed by using bovine SOD (20 U/ml) as a negative control treatment in a well containing xanthine/xanthine oxidase and DHE.

3.3.2 Hydrogen Peroxide Scavenging In Vitro $H_2O_2$-scavenging activity of the PPS microspheres was verified in vitro using an Amplex Red Hydrogen Peroxide/Peroxidase Assay kit according to the manufacturer's instructions. Xanthine and xanthine oxidase were used at the same concentrations as described in the DHE assay to generate a reaction solution containing both superoxide and hydrogen peroxide. The reaction solution was added to wells in a black-walled, 96-well plate containing either PBS, blank PPS microspheres (final concentrations of 60 μg/mL and 7 μg/mL), or free tempo-benzoate (final concentrations of 0.5 mg/mL and 60 μg/mL). The Amplex Red working solution was freshly prepared as described in the kit instructions using the included Amplex Red, horseradish peroxidase, and 1× reaction buffer. The working solution was then added to the wells and fluorescence was measured in a plate reader at 1 hour with an excitation of 530 nm and an emission of 590 nm.

3.3.3 Peroxynitrite Scavenging In Vitro

The ability of PPS microspheres to scavenge peroxynitrite was tested in vitro using a Pyrogallol Red (PGR) bleaching assay. Treatment groups consisting of PBS, blank PPS microspheres (0.5-1.5 mg/mL), tempo-PPS microspheres (0.5 mg/mL), tempol (0.2 mg/mL, hydrophilic analog of tempo-benzoate), and ascorbic acid (negative control, pH adjusted to 7.4) were prepared in a 48-well plate with 500 μL volume per well. A PGR stock solution was prepared in PBS (0.025 μM) and 10 μL was added to each well. Peroxynitrite stock solution was thawed on ice and diluted to a concentration of 1 mM in 0.3 M NaOH. After baseline absorbance of the dye was measured in a plate reader at 540 nm, 5 μL of peroxynitrite was added to each well (final concentration of 10 μM) and absorbance measurements were collected for one hour.

3.4 In Vivo

3.4.1 Diabetes Model Development

Three variations on a Type 1 diabetes model were compared prior to selecting the model for the therapeutic studies. In all three variations, male FVB mice (Jackson Laboratory) were given daily intraperitoneal injections of streptozotocin (STZ, 50 mg/kg) for 5 consecutive days after a 5 hour fast. One group was given STZ at 9 weeks of age and was hyperglycemic for 5 weeks prior to surgical induction of ischemia. The second group was given STZ at 9 weeks of age, but surgery was delayed until 15 weeks of hyperglycemia. The third group was given STZ at 19 weeks of age, and underwent surgery after 5 weeks of hyperglycemia (at same age as second group). The three groups are respectively referred to as the "younger cohort", "older cohort—15 weeks diabetic", and "older cohort—5 weeks diabetic". Non-diabetic mice that were age-matched to the younger and older cohorts at the time of surgery were included to assess the effects of hyperglycemia in each variation of the model. In all groups, glucose levels were measured at the onset of hyperglycemia following the STZ treatment, and again at the time of surgery. Mice with levels above 300 mg/dL were considered diabetic.

3.4.2 Mouse Hind Limb Ischemia Model

After 5 or 15 weeks of hyperglycemia, hind limb ischemia (35) was surgically induced in diabetic and age-matched non-diabetic mice as described previously (26). Briefly, the femoral artery and vein of the right hind limb were ligated with 6-0 sutures proximal to the origins of the superficial epigastric artery and deep branch of the femoral artery, and proximal to the vessels the branch from the femoral artery near the knee. Major side branches were also ligated with 6-0 sutures before the ligated segment of the femoral artery and vein was excised. The incision was closed with interrupted 5-0 nylon sutures. In therapeutic experiments, treatments were injected intramuscularly in the ischemic limb following closure of the skin incision. Treatment injections were administered in a total of 100 μL divided among 3 injection sites in the adductor muscle and 3 injection sites in the gastrocnemius muscle. Surgery was performed under isoflurane anesthesia at normal body temperature. Analgesia was administered subcutaneously pre-operatively and every 24 hours post-operatively until animals exhibited normal appearance and behavior (5-10 mg/kg ketoprofen). Mice were fed a standard chow diet ad libitum with free access to water. All protocols were approved by the Institutional Animal Care and Use Committee of Vanderbilt University and done in accordance with the National Institute of Health's *Guide for the Care and Use of Laboratory Animals*.

3.4.3 ROS Measurement in Extracted Muscle Tissue

After 8 or 14 days of ischemia, the gastrocnemius and adductor muscles were extracted immediately post-mortem and dissected pieces of tissue were weighed and transferred into Krebs HEPES Buffer (pH 7.35) on ice. Amplex Red working solution was prepared using components from the Molecular Probes Amplex Red Hydrogen Peroxide/Peroxidase Assay kit as follows: 1 vial of Amplex Red (154 μg) was dissolved in 60 μL DMSO and added to 11.82 mL of Krebs HEPES Buffer along with 120 μL of horseradish peroxidase (from a stock solution of 10 U/ml in 0.05 M sodium phosphate at pH 7.4). 300 μL of working solution was added to each well in a 48-well plate. Tissue samples were transferred into the Amplex Red solution and incubated in the dark for 1 hour at 37° C. Tissue samples weighing approximately 20 mg were used to ensure proper $H_2O_2$ diffusion out of the tissue. A standard curve of hydrogen peroxide was prepared in a black-walled 96-well plate at the same time that the tissue incubation began. After 1 hour, 150 µL of solution from each sample was transferred to the black 96-well plate and Amplex Red fluorescence was measured on an IVIS imaging system (Lumina Series III, PerkinElmer) with 530/590 nm excitation/emission filters. Tissue hydrogen peroxide concentration was normalized to tissue mass, and ischemic limb values were normalized to the contralateral control muscle for each animal.

3.4.4 Hyperspectral Imaging of Hemoglobin Oxygen Saturation

Hemoglobin oxygen saturation (HbSat) was measured in the footpads of the hind limbs using hyperspectral imaging as described previously (26, 36) at days 0, 3, 7, 14, 21, and 28 post-surgery. Briefly, diffuse reflectance images were collected in the visible light range from 500 to 620 nm in 8-nm increments using a liquid crystal tunable filter (CRi, Inc.) mounted on a cooled CCD camera (Andor, 1392×1040 pixel) with a variable focal length camera lens (Navitar, f=18-108 mm). Illumination was provided by a halogen lamp. HbSat was calculated for each image pixel using a modified version of Beer's law (36-38). Average HbSat values were computed for each footpad, and the ischemic footpad HbSat was normalized to that of the contralateral footpad for each animal.

3.4.5 Perfusion Imaging

Perfusion images of the footpads were acquired at days 0, 3, 7, 14, 21, and 28 post-surgery with a laser Doppler perfusion imager (LDPI) (Perimed PeriScan PIM II). An average perfusion value was computed for each footpad, and the data are presented as the ratio of the ischemic footpad perfusion to that of the control footpad for each animal.

3.4.6 Intravital Imaging of Vascular Morphology with Optical Coherence Tomography At 0, 3, 7, 14, 21, and 28 days post-surgery, the hind limb vasculature in the adductor and gastrocnemius muscle regions was imaged using a swept-source optical coherence tomography (OCT) system as described previously (26, 39). The OCT system has a 100 kHz source with a center wavelength of 1060 nm (Axsun Technologies, Inc.). Speckle variance OCT volumes were acquired non-invasively through the skin in 4 mm×4 mm areas covering the two muscle regions, and average intensity projections in depth were used to visualize all vessels detected within the imaged volume. After image processing was performed to enhance contrast and enable vessel segmentation (39, 40), morphological parameters including vessel area density (total area filled by vessels/total area of imaged region) and vessel length fraction (total vessel length/total area of imaged region) were quantified.

3.4.7 Histological Evaluation of Response to Microspheres

A subset of mice from each treatment group was sacrificed at day 8 post-surgery. The gastrocnemius and adductor muscles were removed, and a portion of each muscle was fixed with 10% formalin for 24 hours and embedded in formalin. Histological sections (5 µm) were cut for CD68 (MCA1957, Bio-Rad, Raleigh, N.C.) and nitrotyrosine (AB5411, Millipore, Billerica, Mass.) immunohistochemistry (Supplemental Methods in Appendix B).

3.5 Statistical Analysis

All data are reported as mean±standard error of the mean (SEM). Kruskal-Wallis Analysis of Variance (ANOVA) with a post-hoc Tukey test for multiple comparisons was used to determine treatment effects and $p<0.05$ was considered significant. For comparisons between only two groups, a Wilcoxon Rank Sum test was used. For longitudinal imaging endpoints, an ANOVA general linear model analysis was performed to model the response curves and compare treatment effects at each time point. $p<0.05$ was considered significant.

4. Results 4.1 Microsphere Synthesis and Characterization 4.1.1 Synthesis and Characterization of PPS PPS was synthesized by anionic polymerization of propylene sulfide as described previously (29) and depicted in Suppl. FIG. B.1. The molecular weight and polydispersity of PPS as determined by GPC were $M_n$=5000 g/mol and PDI=1.3, respectively. The polymer structure was confirmed by $^1$H NMR spectra recorded in $CDCl_3$: 1.3-1.4 (s, $CH_3$), 2.5-2.8 (s, —CH), 2.8-3.1 (s, $CH_2$), 3.72 (t, $CH_2$—OH).

4.1.2 Microsphere Characterization

Tempo-benzoate incorporation efficiency in the microspheres was quantified using HPLC to measure tempo-benzoate concentration in dissolved microspheres. Drug content was 5.5% w/w tempo-benzoate/microspheres and drug encapsulation efficiency was 71% (average of 2 independent batches of microspheres).

4.2 ROS-Scavenging In Vitro

ROS-dependent drug release from the PPS microspheres upon exposure to both $H_2O_2$ and peroxynitrite has been previously demonstrated by our lab using curcumin as a model hydrophobic drug (26). Here, the ROS-scavenging activity of the microspheres and the encapsulated tempo-benzoate was evaluated using assays for detection of superoxide, hydrogen peroxide, and peroxynitrite (indirectly through bleaching activity).

4.2.1 Free and Encapsulated Tempo-Benzoate Scavenge Superoxide In Vitro

The superoxide scavenging activity of the tempo-PPS microspheres was evaluated in a cell free xanthine/xanthine oxidase system using DHE oxidation as a marker of superoxide (33). Compared to no treatment, blank PPS microspheres do not reduce the fluorescent signal from the DHE oxidation product, while both free tempo-benzoate and tempo-PPS microspheres significantly reduce fluorescence (FIG. 10A) (one-way ANOVA $p<0.0001$). The fluorescent signal is further inhibited in the presence of SOD as a negative control (data not shown).

4.2.2 PPS Microspheres Scavenge $H_2O_2$ In Vitro

The $H_2O_2$-scavenging activity of PPS was confirmed using Amplex Red as a reporter molecule in a xanthine/xanthine oxidase system that produces both superoxide and $H_2O_2$. Treatment with blank PPS microspheres significantly reduces Amplex Red fluorescence, while treatment with free tempo-benzoate significantly increases the fluorescent signal after 1 hour of incubation as tempo-benzoate converts superoxide into $H_2O_2$ (FIG. 10B) (one-way ANOVA $p<0.001$).

Figure 11:
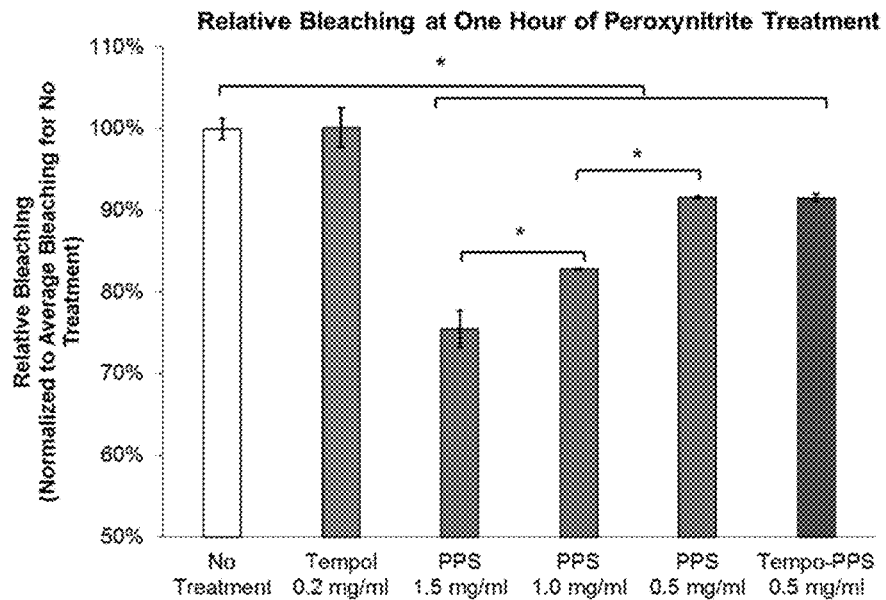
FIG. 11: Blank PPS and tempo-PPS microspheres protect PGR from bleaching by peroxynitrite in a dose-dependent manner (one-way ANOVA p<0.0001, *significant post-hoc comparisons). Doses are presented as microsphere mass/volume. Data presented as mean±SD

4.2.3 PPS Microspheres have Peroxynitrite Scavenging Activity that Protects PGR from Bleaching Pyrogallol Red is bleached in the presence of peroxynitrite, and this bleaching effect can be reduced or inhibited by antioxidant compounds such as ascorbic acid (41). In the presence of blank-PPS and tempo-PPS microspheres, PGR is protected from bleaching in a dose-dependent manner (FIG. 11, one-way ANOVA $p<0.0001$). Ascorbic acid was tested as a negative control and resulted in only 2% relative bleaching (nearly complete protection for PGR from peroxynitrite).

4.3 Diabetes Model Characterization

Three variations on an STZ-induced model of Type 1 diabetes were compared prior to selecting a model for therapeutic studies with tempo-PPS microspheres. The three variations consisted of 5 weeks of hyperglycemia in a younger cohort, 15 weeks of hyperglycemia in an older cohort, and 5 weeks of hyperglycemia in an older cohort (same age as group with 15 weeks of hyperglycemia). Age-matched, non-diabetic mice were included in both the younger and older cohorts.

4.3.1 Hemoglobin Saturation and Perfusion Recovery in Diabetes Models

Figures 12A, 12B, 12C, 12D:
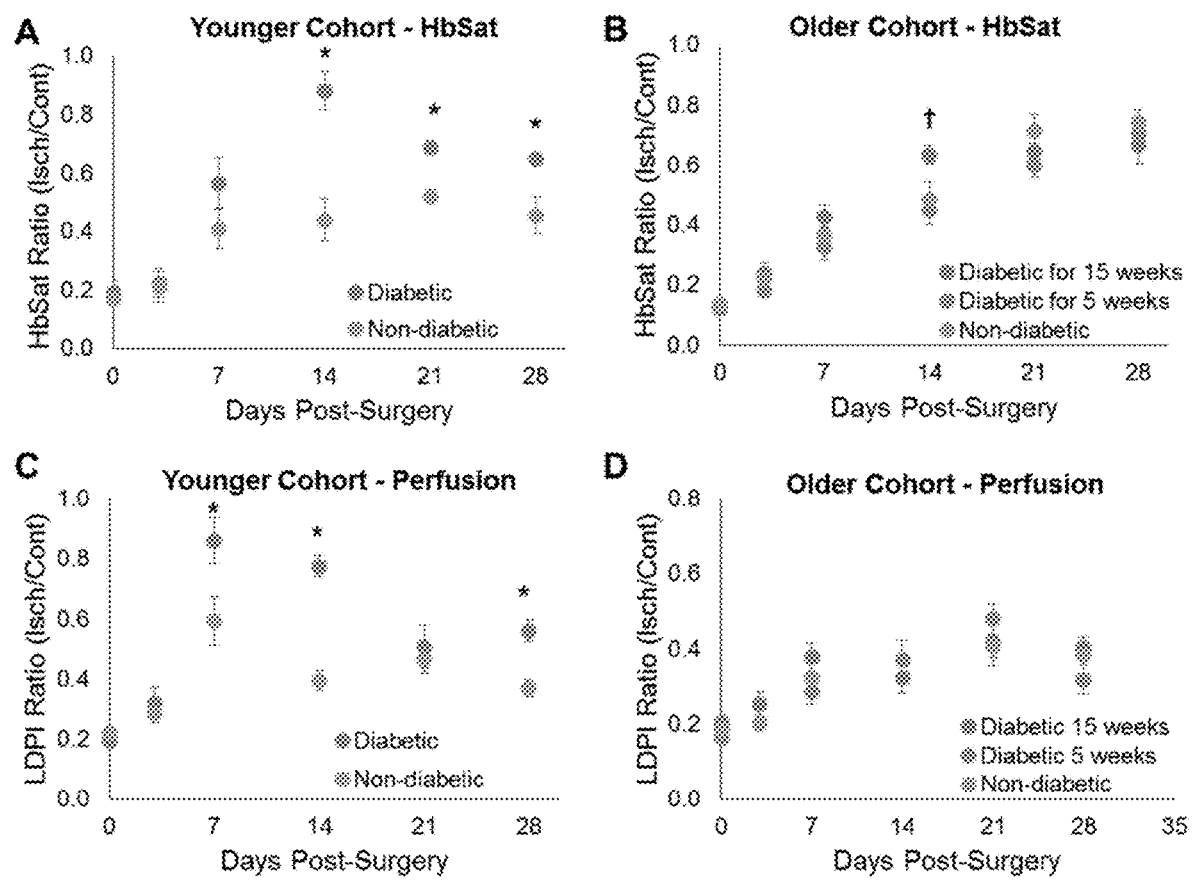
FIGS. 12A-12D: Oxygenation and perfusion outcomes of diabetic and non-diabetic mice with hind limb ischemia. Younger diabetic mice exhibit an early "overshoot" response in hemoglobin saturation and perfusion measurements in the footpads that is absent from the response to ischemia in older diabetic mice.

Longitudinal recovery of hemoglobin oxygen saturation (HbSat) in the footpads was measured using hyperspectral imaging. In the younger cohort, the diabetic mice responded to ischemia with a significant "overshoot" response in comparison to the age-matched non-diabetic mice ($p<0.05$ with a rank sum test at days 14, 21, and 28). This response peaks at day 14 and is followed by regression in the HbSat ratio (FIG. 12A). In contrast, the older cohort does not have any significant differences between groups with the exception of a higher HbSat ratio in the group with 15 weeks of hyperglycemia at day 14 ($p<0.05$ between 15-week diabetic mice and 5-week diabetic mice), and the HbSat ratio is highest at day 28 post-surgery (FIG. 12B).

The footpad perfusion ratio was imaged over time using LDPI. In the younger cohort, an early overshoot response is apparent in the diabetic mice ($p<0.05$ at days 7, 14, and 28 compared to non-diabetic, age-matched mice) (FIG. 12C). In a manner similar to the HbSat response, this overshoot peaks early in the time course (day 7) and is followed by regression of the LDPI ratio. In the older cohort of mice, there are no significant differences between the groups at any point in the time course, and the LDPI ratio peaks at day 21 (FIG. 12D).

4.3.2 Non-Invasive Imaging of Vascular Morphology in Diabetes Models

Figures 13A, 13B, 13C, 13D:
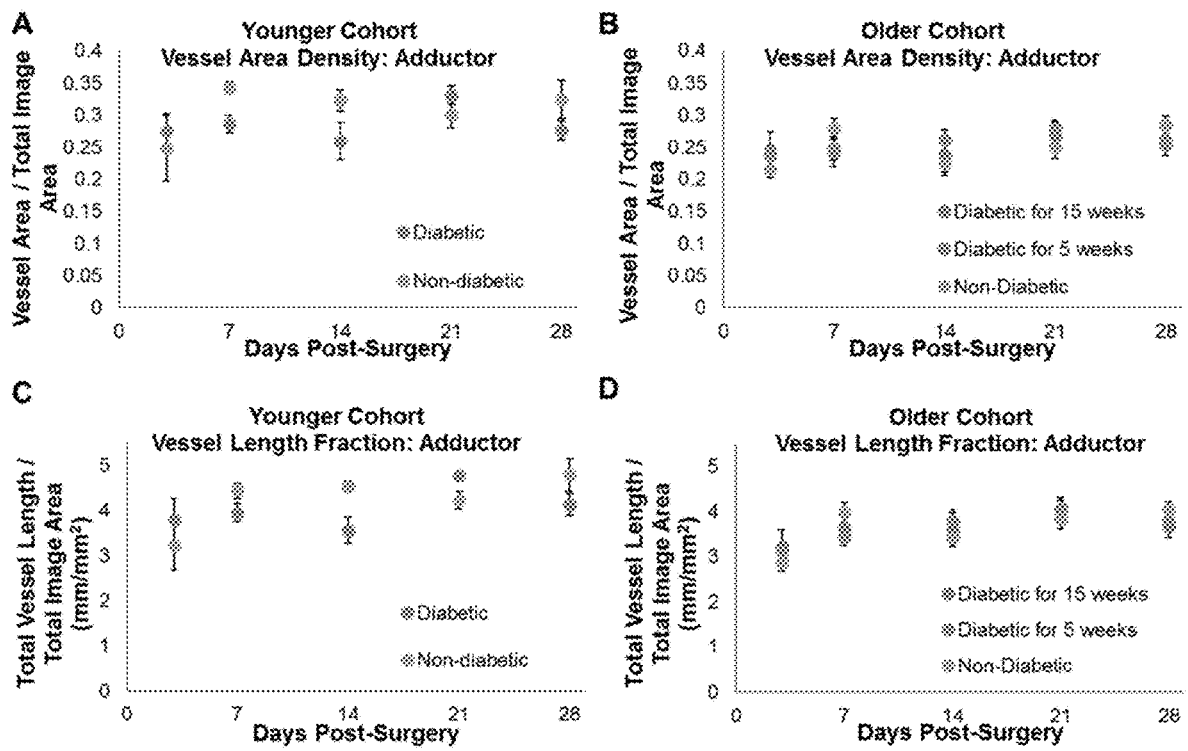
FIGS. 13A-13D: Vascular morphology parameters from intravital OCT images reveal differences between diabetes models. In the younger cohort, there is a trend toward increased vessel area density (FIG. 13A) and vessel length fraction (FIG. 13C) in the non-diabetic mice at days 7 and 14 (p-value at minimum for n=3/group). In the older cohort, there are no significant differences between groups in vessel area density (FIG. 13B) or vessel length fraction (FIG. 13D). n=3/group for younger cohort and n≥6/group for older cohort.

The vasculature in the proximal limb (adductor muscle region) was imaged non-invasively in the younger and older cohorts of diabetic and non-diabetic mice using OCT. In the younger cohort, there is a trend toward greater vessel area density and vessel length fraction in the non-diabetic mice at days 7 and 14 post-surgery (p-value for rank sum test at day 7 is at minimum value for n=3/group) (FIGS. 13A & C). In the older cohort, there are no significant differences in vessel area density or length fraction between the diabetic and non-diabetic mice (FIGS. 13B & D). Additionally, there is a trend toward increased vessel area density and vessel length fraction in the younger mice in comparison to the older mice. At day 7, vessel area density in the younger, non-diabetic group is greater than that in the older mice with 5 or 15 weeks of diabetes (Kruskal-Wallis ANOVA $p=0.05$).

Figures 14A, 14B:
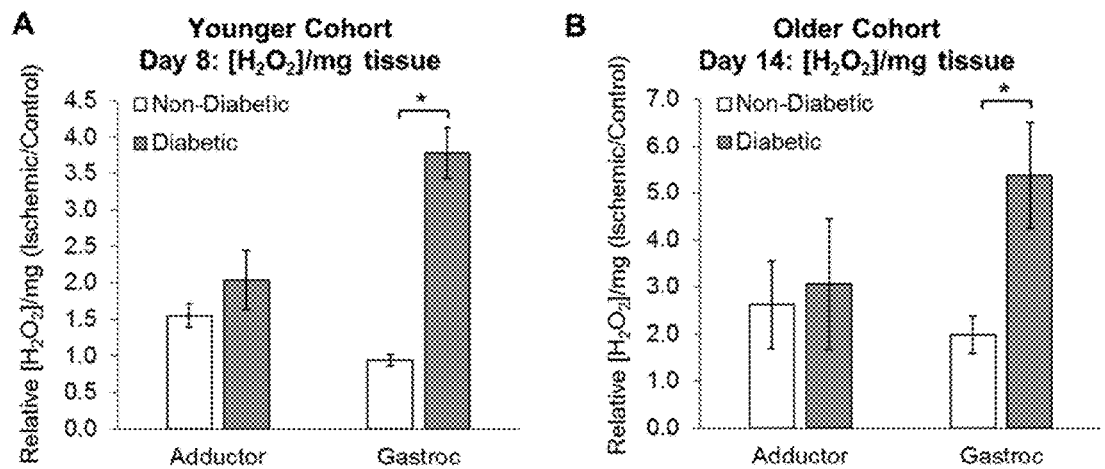
FIGS. 14A-14B: Tissue $H_2O_2$ levels were measured in freshly excised gastrocnemius and adductor muscles in diabetic and age-matched non-diabetic mice.

4.3.3 $H_2O_2$ is Elevated in Response to Ischemia in Diabetic Mice Relative to Non-Diabetic Mice Tissue $H_2O_2$ was measured in freshly excised adductor and gastrocnemius muscles in both cohorts of mice using the Amplex Red assay. In the younger cohort, $H_2O_2$ is elevated in ischemic limbs relative to control limbs in the adductor in both groups and in the gastrocnemius for the diabetic mice at day 8 post-surgery (ischemic/control>1) (FIG. 14A). The relative $H_2O_2$ level (ischemic/control ratio) is significantly greater in the gastrocnemius muscle of diabetic mice compared to that of the non-diabetic mice ($p<0.05$). In the older cohort, $H_2O_2$ is elevated in both ischemic adductor and gastrocnemius muscles relative to control limbs in both diabetic and non-diabetic mice at day 14 post-surgery (FIG. 14B). The relative $H_2O_2$ level is significantly greater in the gastrocnemius muscle of diabetic mice than that of non-diabetic mice in the older cohort ($p<0.05$).

4.4 Response to PPS and Tempo-PPS Microspheres in Long-Term Hyperglycemic Mice

Based on the presence of a larger "therapeutic window" for improving the vascular response at earlier time points in the older cohort of mice, the variation of the diabetes model consisting of 15 weeks of hyperglycemia prior to surgery was selected for subsequent therapeutic studies. Additionally, these diabetic mice demonstrated elevated oxidative stress in the ischemic limb relative to age-matched non-diabetic mice, as measured by the Amplex Red assay for $H_2O_2$.

4.4.1 Functional Response to Two Microsphere Doses In Vivo

Figures 15A, 15B, 15C, 15D:
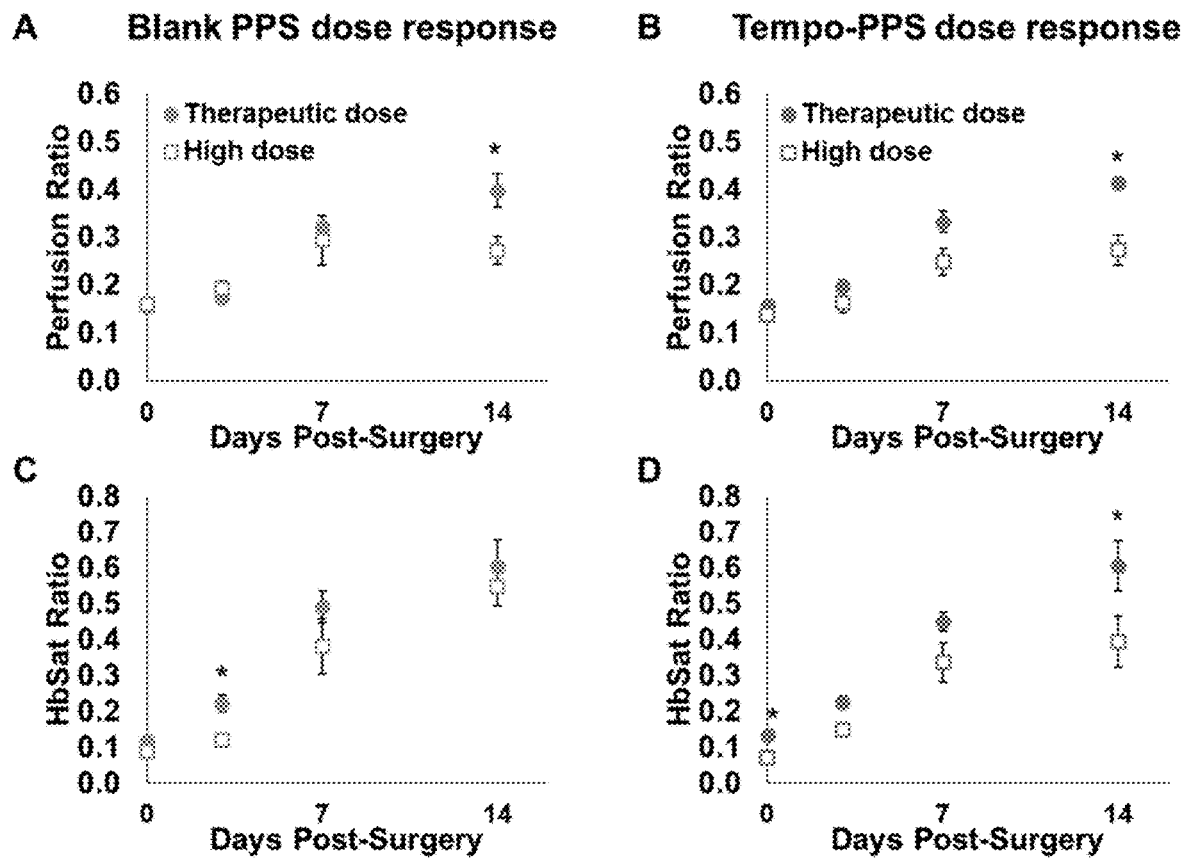
FIGS. 15A-15D: Two doses of microspheres were compared using functional measures of recovery. The "therapeutic" dose contains 1.2 mg of PPS (plus 0.03 mg tempo-benzoate in tempo-PPS), and the "high" dose contains 4.75 mg of PPS (plus 0.15 mg tempo-benzoate in tempo-PPS). The perfusion ratio (FIG. 15A-FIG. 15B) for the therapeutic dose of both blank PPS and tempo-PPS is significantly greater than that of the high dose of the respective treatment at day 14 (*p<0.05) (and p<0.1 for tempo-PPS comparison for day 7). The HbSat ratio (FIG. 15C-FIG. 15D) for the therapeutic dose is significantly greater than that of the high dose at day 3 for blank PPS and at days 0 and 14 for tempo-PPS (*p<0.05). (p<0.1 at day 3 for tempo-PPS HbSat). n≥5/group.

Two doses of blank and tempo-PPS microspheres were tested in the ischemic limb of diabetic mice. Microsphere doses containing 1.2 mg or 4.75 mg of PPS (plus 0.03 mg or 0.15 mg of tempo-benzoate, respectively, in the tempo-PPS cohort) were injected in the ischemic limb at the time of surgery, and hyperspectral imaging and LDPI were performed to assess the functional response over 2 weeks (FIG. 15). In both measures of recovery, the higher dose of microspheres tended to impair the vascular response to ischemia. The perfusion ratio for the lower dose, referred to as the therapeutic dose, is significantly greater than that of the high dose of the respective treatment at day 14 ($p<0.05$) (FIG. 15A-B). At day 7, there is a trend toward increased perfusion ratio in the tempo-PPS therapeutic dose group compared to the high dose group ($p<0.1$). The HbSat ratio shows a similar trend of an improved response in the therapeutic dose group for both treatments (FIG. 15C-D). The HbSat ratio for the therapeutic dose is significantly greater at day 3 for blank PPS and at days 0 and 14 for tempo-PPS ($p<0.05$).

4.4.2 High-Dose Microsphere Treatment Reduces $H_2O_2$ in Ischemic Muscle

Figures 16A, 16B:
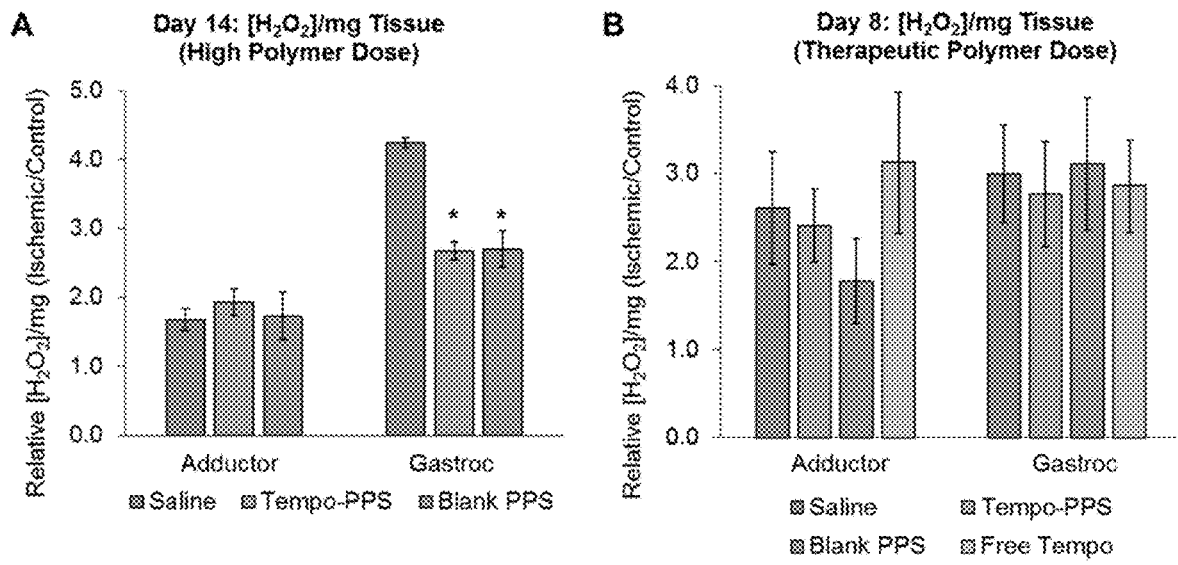
FIGS. 16A-16B: The effect of microspheres on $H_2O_2$ levels in ischemic muscle was measured using the Amplex Red assay.

Tissue $H_2O_2$ was measured in freshly excised adductor and gastrocnemius muscles at day 14 for mice treated with the high dose of PPS microspheres or tempo-PPS microspheres and compared to mice receiving a saline injection as a vehicle control (FIG. 16A). At the high dose of microspheres, relative $H_2O_2$ in the gastrocnemius muscle is significantly reduced in comparison to saline-treated control mice ($p<0.05$). At the lower dose of microspheres which resulted in improved functional recovery (FIG. 15), no significant differences in relative $H_2O_2$ between treatment groups at day 8 were detectable using the Amplex Red assay.

Figures 17A, 17B:
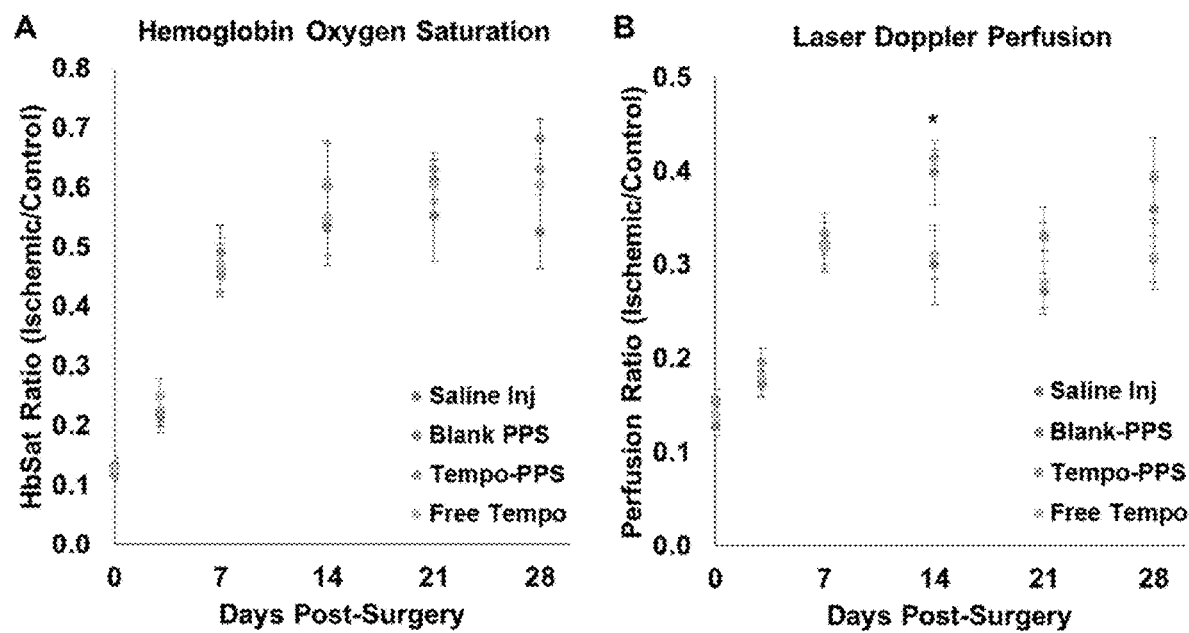
FIGS. 17A-17B: HbSat and perfusion were measured in the footpads of diabetic mice treated with saline, blank PPS, tempo-PPS, or free tempo-benzoate.

4.4.3 Distal Response to Microsphere Treatment Measured with Hyperspectral Imaging and LDPI Hemoglobin oxygen saturation was measured in the footpads of diabetic mice treated with saline, blank PPS, tempo-PPS, or free tempo at the time of hind limb ischemia surgery (FIG. 17A). Microspheres were administered at the therapeutic dose identified in the dose response experiment described previously (FIG. 15). Individual time point analyses based on the raw data did not identify significant differences between treatment groups; however, a t-test performed on the general linear model of the longitudinal response curves shows that the blank PPS and saline-treated groups differ significantly from days 19 to 28 ($p<0.05$). The perfusion ratio was also measured to assess the effect of microsphere treatments on the response to ischemia (FIG. 17B). At day 14, the perfusion ratio for the tempo-PPS group is significantly greater than that for the saline and free tempo groups, and the blank PPS group perfusion ratio is significantly greater than that of the free tempo group as determined by a Kruskal-Wallis ANOVA (*p<0.05) and a post-hoc multiple comparisons test. Similarly, a t-test performed on the longitudinal response curves generated by a general linear model analysis returns significantly higher perfusion ratios for the microsphere-treated groups compared to the saline and free tempo groups for the latter half of the time course.

Figure 18:
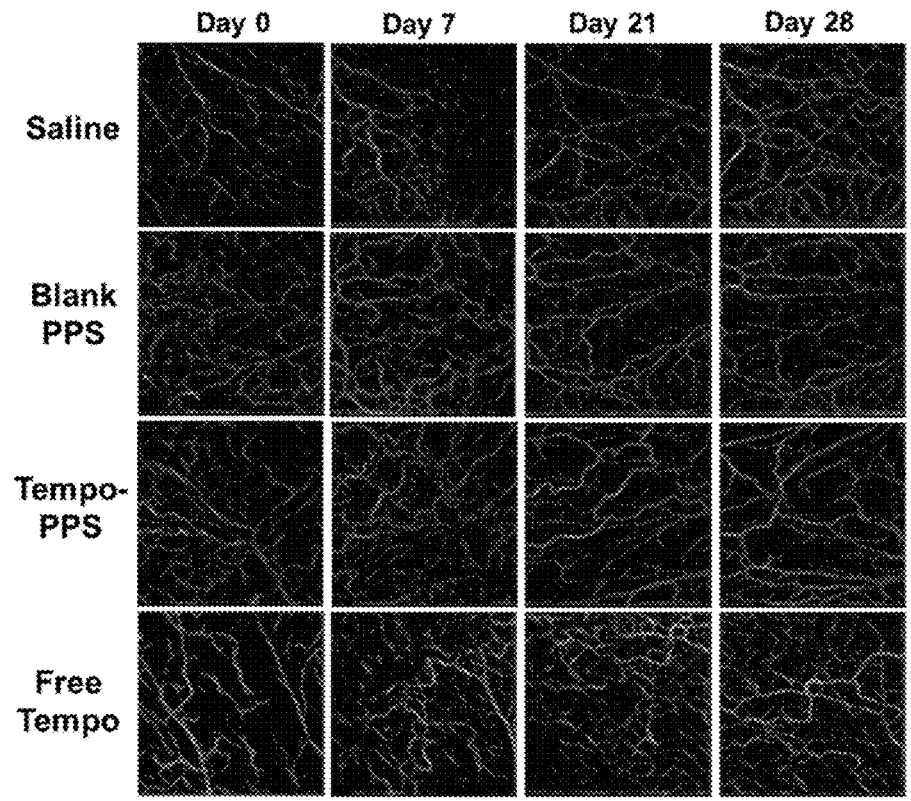
FIG. 18: Representative time course images of vascular morphology in the adductor muscle region for each treatment group. Images are projections of all vessels present in the volume acquired over a 4 mm×4 mm area.
Figure 19:
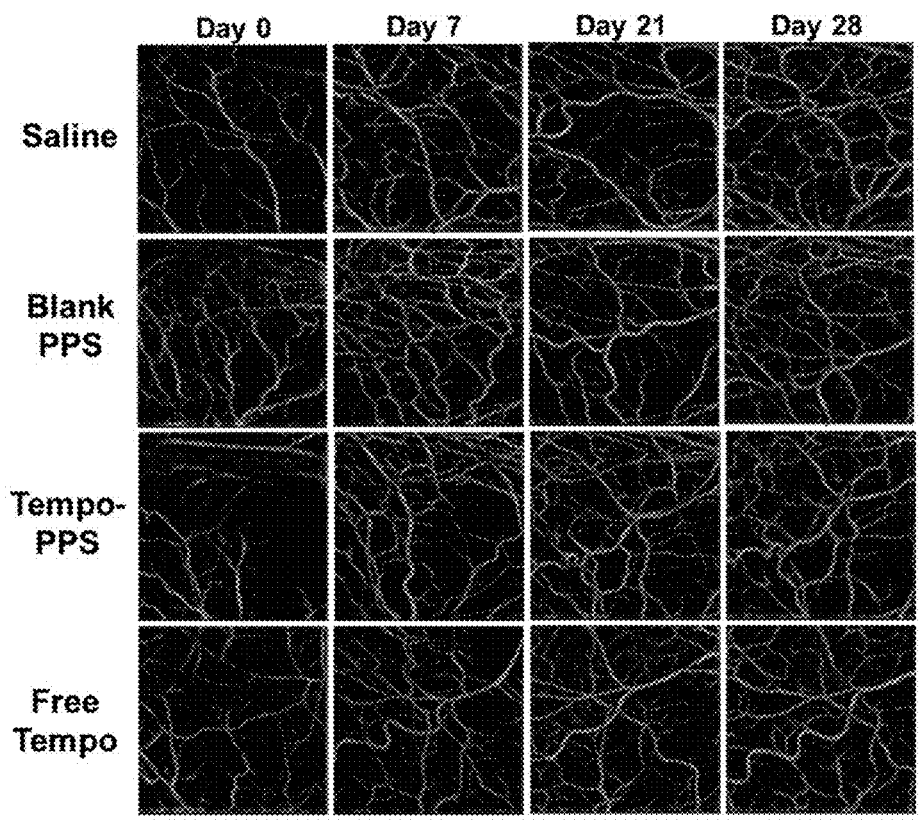
FIG. 19: Representative time course images of vascular morphology in the gastrocnemius muscle region for each treatment group. Images are projections of all vessels present in the volume acquired over a 4 mm×4 mm area.

4.4.4 Non-Invasive Imaging of Vascular Morphology Changes in Response to Therapy Speckle variance OCT (39, 40) was used to image the longitudinal vascular response to microsphere therapies in the adductor and gastrocnemius muscle regions. Representative time course images from one animal in each treatment group are given for the adductor and gastrocnemius regions in FIG. 18 and FIG. 19, respectively.

Figures 20A, 20B:
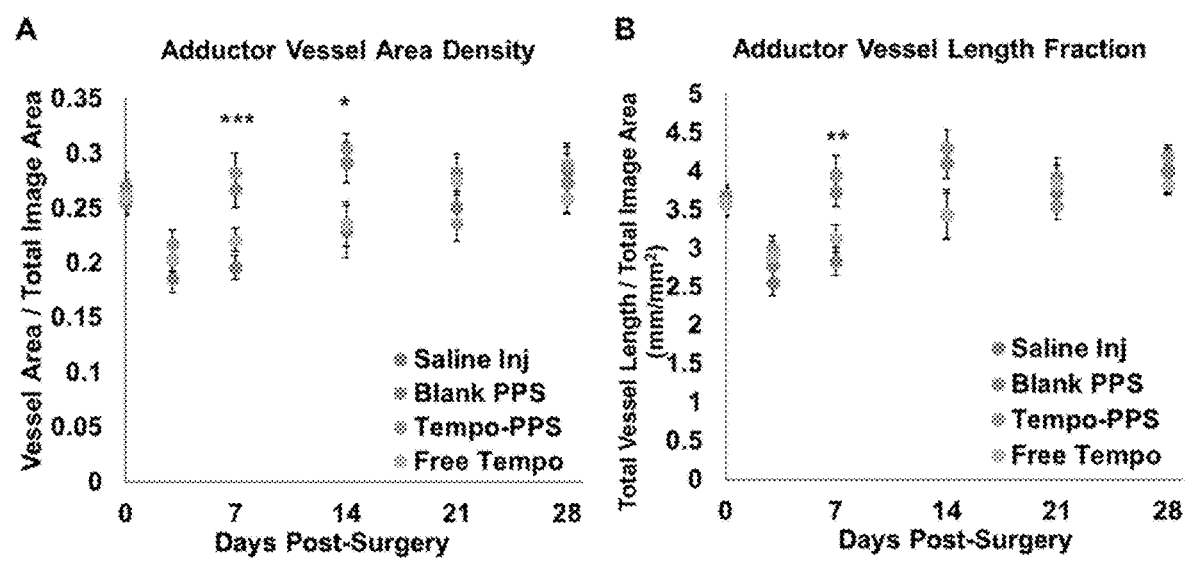
FIGS. 20A-20B: Vessel morphology parameters were quantified from OCT images of the adductor muscle region. At day 7, vessel area density (FIG. 20A) is significantly lower in the saline group than in both blank PPS and tempo-PPS groups (Kruskal-Wallis ANOVA ***p<0.001). At day 14, vessel area density in the tempo-PPS group is significantly greater than that in the saline and free tempo groups (Kruskal-Wallis ANOVA *p<0.05). Vessel length fraction (FIG. 20B) differs significantly at day 7 between the saline and both microsphere groups, and between the free tempo and tempo-PPS groups (Kruskal-Wallis ANOVA **p<0.01). At day 14 a trend toward increased vessel length fraction in microsphere-treated groups persists (p<0.1). n=15-20/group for days 0-7 and n=6-7/group for days 14-28.

In the adductor muscle, vessel area density is significantly greater in microsphere-treated groups at day 7 (p<0.001) and day 14 (p<0.05) relative to the saline and free tempo groups (FIG. 20A), and vessel length fraction is significantly greater at day 7 (p<0.01) (FIG. 20B).

Figures 21A, 21B:
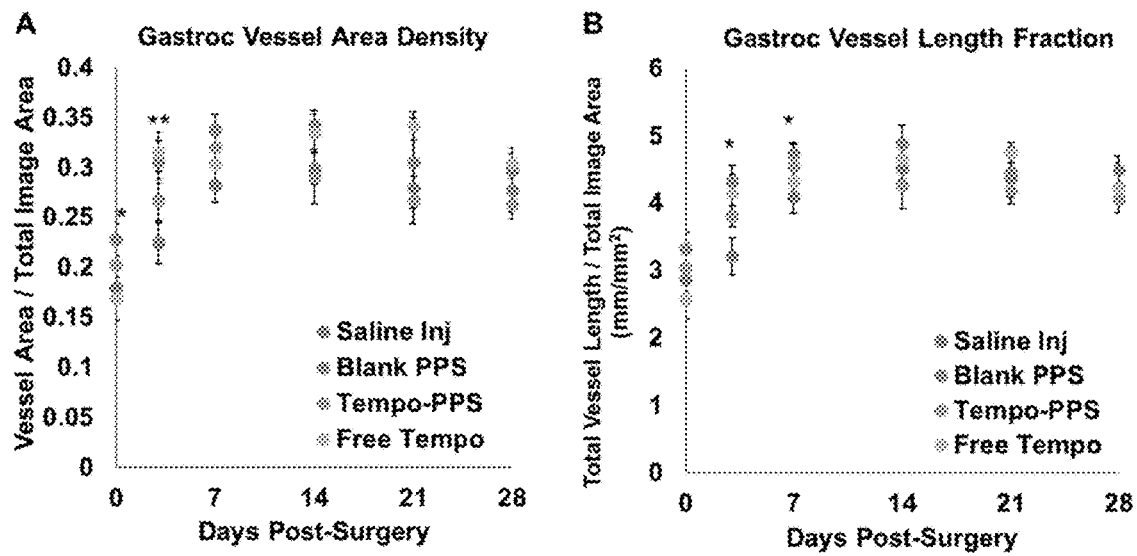
FIGS. 21A-21B: Vessel morphology parameters were quantified from OCT images of the gastrocnemius muscle region. At day 0, the blank PPS group has significantly greater vessel area density (FIG. 21A) than the saline and free tempo groups (Kruskal-Wallis ANOVA *p<0.05). At day 3, vessel area density in the saline group is significantly lower than that in the blank PPS and free tempo groups (Kruskal-Wallis ANOVA *p<0.01). Vessel length fraction (FIG. 21B) is significantly lower in the saline group than in the blank PPS and free tempo groups at day 3 (Kruskal-Wallis ANOVA *p<0.05). At day 7, saline-treated mice have significantly lower vessel length fraction than the blank PPS and tempo-PPS groups (Kruskal-Wallis ANOVA *p<0.05). n=15-20/group for days 0-7 and n=6-7/group for days 14-28.

In the gastrocnemius muscle, vessel area density is significantly lower in the saline and free tempo-treated groups at day 0 relative to the blank PPS group (p<0.05) (FIG. 21A). At day 3, saline-treated mice have significantly lower vessel area density than the blank PPS and free tempo groups (p<0.01). Similarly, vessel length fraction in the gastrocnemius muscle is significantly lower in the saline group than that in the blank PPS and free tempo-treated groups at day 3 (p<0.05). At day 7, saline-treated mice have significantly lower vessel length fraction than the blank PPS and tempo-PPS treated groups (p<0.05).

Figure 22:
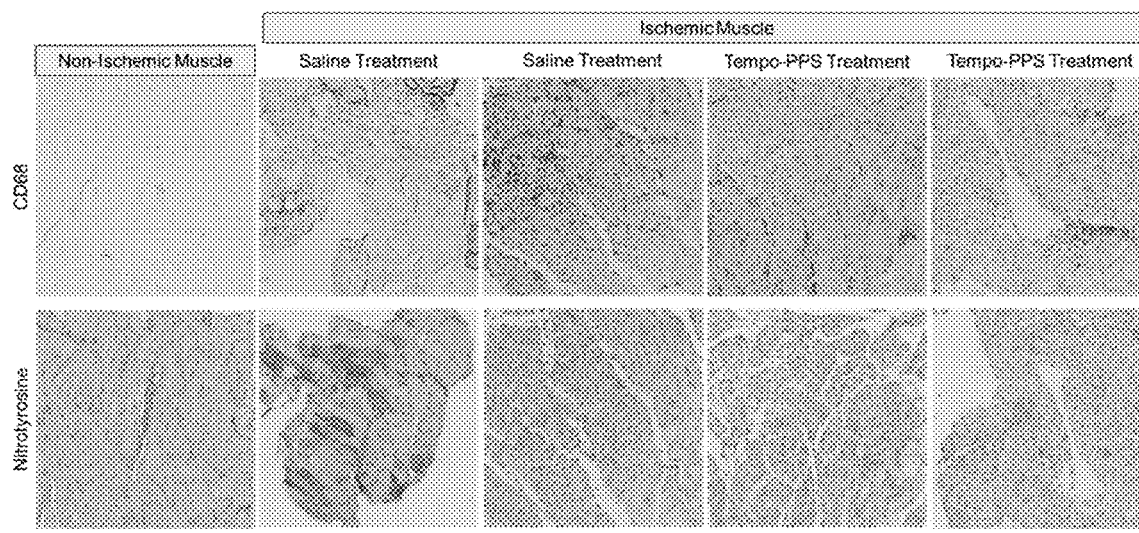
FIG. 22: CD68 and nitrotyrosine IHC were performed on gastrocnemius muscles (5 µm sections) extracted at day 8 post-surgery. Staining for macrophages and nitrotyrosine (oxidative stress-induced damage) is present in ischemic muscles in all treatment groups, and the extent of inflammation and damage is variable within treatment groups.

4.4.5 IHC for Assessing Inflammation and Oxidative Stress in the Ischemic Muscle CD68 IHC on sections from gastrocnemius muscles excised at day 8 post-surgery (FIG. 22, top) show that macrophage infiltration is present in ischemic tissue in all treatment groups. The extent of inflammation is variable within all treatment groups which may be attributable to sampling and/or inter-animal variability. Nitrotyrosine IHC was performed in serial sections in order to assess peroxynitrite-mediated oxidative stress in the ischemic gastrocnemius (FIG. 22, bottom). In a non-ischemic control muscle, CD68 staining is sparse and nitrotyrosine staining is absent. In ischemic muscles, nitrotyrosine staining is present in varying intensities and does not appear to correlate with the extent of CD68 staining. These observations suggest that both inflammation and oxidative stress are present in ischemic muscles across treatment groups, but a larger sampling volume of tissue is needed to provide quantification of oxidative stress for discerning treatment effects.

5. Discussion of Example 2

Transient or low levels of ROS are important to signaling pathways that promote regeneration and growth, while chronic or high levels of ROS, which often occurs in diabetes, can be detrimental to vascular function. The inhibition of ROS in healthy animals has shown that ROS have an overall proangiogenic function. However, studies using preclinical models of chronic oxidative stress (i.e. diabetic animals) have demonstrated the potential for antioxidant treatment to improve neovascularization and vascular function in these situations. Diabetes is a known risk factor for atherosclerosis and is associated with increased prevalence of PAD, so the development of more effective treatments for mitigating vascular dysfunction is of significant interest. Scavenging ROS with superoxide dismutase and/or catalase mimetics is a promising approach, but to date these treatments have generally been administered systemically in preclinical models. In order to avoid off-target effects in tissues with physiologically appropriate levels of ROS, we have pursued ROS-sensitive PPS microspheres as a local delivery vehicle for superoxide dismutase mimetic tempo-benzoate.

Figure 10:
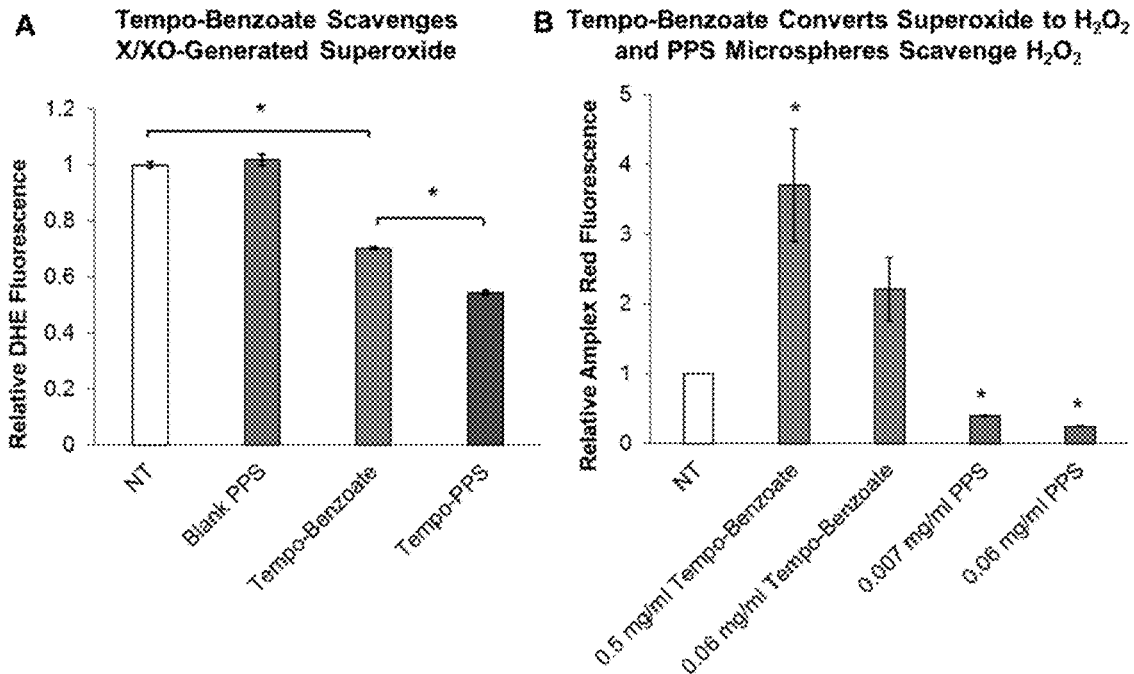
FIG. 10: Free and encapsulated tempo-benzoate scavenge superoxide, while blank PPS microspheres scavenge $H_2O_2$ in vitro.

PPS was selected as the polymer carrier in this application because it provides ROS-responsive drug release, scavenges $H_2O_2$ (FIG. 10B) and peroxynitrite (FIG. 11), and protects cells from $H_2O_2$-induced toxicity. Additionally, this dual-antioxidant approach allows for PPS to scavenge the $H_2O_2$ generated by the dismutation of superoxide by encapsulated tempo-benzoate (FIGS. 10A & 10B). This effect of combined ROS targeting has been previously demonstrated in vitro in a hybrid polymer-enzyme nanocarrier system. However, micron-sized particles such as the PPS microspheres are advantageous because they are able to form a stable depot at the targeted site and provide sustained drug release over a longer time frame as shown in previous work.

Prior to evaluating the effect of the tempo-PPS microspheres on recovery from hind limb ischemia, we optimized our preclinical model through comparisons between younger mice with 5 weeks of pre-surgical STZ-induced hyperglycemia and older mice with 15 or 5 weeks of hyperglycemia prior to surgery. The duration of hyperglycemia prior to experimental manipulation varies among previously reported preclinical studies of the vascular response to ischemia; however, the effects of diabetes on vascular function have been shown to be disease duration-dependent. Additionally, susceptibility to STZ and the severity of the resulting hyperglycemia and other symptoms varies with mouse strain. In the current work, we have used the FVB strain which is susceptible to robust, persistent hyperglycemia after a low dose STZ protocol (fasting blood glucose ranging from 300-700 mg/dL in the current studies) and has demonstrated improved neovascularization with antioxidant and anti-inflammatory therapies. After induction of hind limb ischemia in the younger and older cohorts of diabetic mice and age-matched non-diabetic controls, an "overshoot" response was observed in footpad hemoglobin saturation and perfusion ratios in the younger diabetic group, but not in the younger non-diabetic group or the older groups (FIG. 13). This response with an early peak followed by regression in the younger diabetic group is similar to that observed in diabetic C57Bl6/J mice which had more pronounced vessel growth and vessel rarefaction phases in comparison to non-diabetic controls. In contrast, the older cohort of mice in the current study did not show significant differences in the footpad measures of recovery, except for a transient increase in the HbSat ratio for the 15 weeks-diabetic group at day 14 (FIG. 12B). As a measure of the vascular response in the proximal limb, vessel morphology parameters were extracted from OCT speckle variance images. There was a trend toward increased vessel density and total length in the adductor muscle region of younger non-diabetic mice, and the older cohort exhibited less vascular remodeling overall in comparison to the younger cohort (FIG. 13). Although there were no significant differences between the older groups in vessel morphology in the adductor, vessel area density and length fraction in the gastrocnemius muscle were significantly lower in the mice with 15 weeks of diabetes compared to the other age-matched groups. Additionally, relative $H_2O_2$ levels were significantly increased in the gastrocnemius of 15 weeks-diabetic mice in the older cohort (FIG. 14B). Taken together, these comparisons indicate that the mice in the older cohort with 15 weeks of diabetes prior to surgery have the greatest "therapeutic window" for reducing oxidative stress in the muscle and improving the vascular response at early time points. Therefore, this model was selected to evaluate the effect of the tempo-PPS microspheres on the response to hind limb ischemia.

Figure 23:
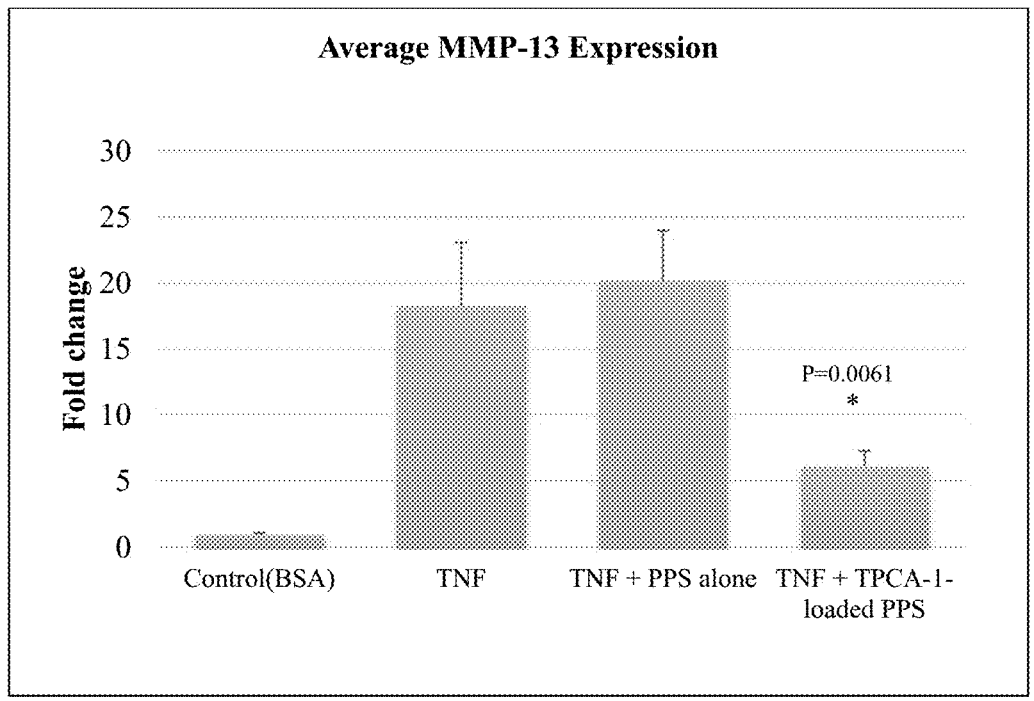
FIG. 23: Average MMP-13 expression from PCR. TNF-α resulted in a marked increase in MMP-13 expression with no change in blank PPS administration. A significant change was achieved using TPCA-1-PPS (p-0.0061).

The functional effects of PPS and tempo-PPS microspheres were evaluated in the hind limb ischemia model using perfusion, hemoglobin oxygen saturation, vessel morphology, and oxidative stress as endpoints. A preliminary dose experiment was performed to identify an appropriate level of ROS-scavenging, since there is an optimal range in which ROS are beneficial to angiogenesis, and scavenging "too much" could be detrimental even in the diabetic model. The comparison of two doses showed that a higher dose of microspheres reduced the perfusion and HbSat ratios significantly (FIG. 15), which is likely due to scavenging $H_2O_2$ to a greater extent (FIG. 16A) in comparison to a low dose of microspheres. In contrast, the lower dose of microspheres (referred to as the therapeutic dose) did not result in a decrease in $H_2O_2$ relative to control groups detectable by the Amplex Red assay (FIG. 16B). However, in subsequent experiments with the therapeutic dose, there were significant increases in perfusion in the footpads (FIG. 17) and vessel remodeling in the adductor (FIG. 21) associated with the microsphere treatments relative to saline and free tempobenzoate controls. Hemoglobin saturation ratios showed a slight improvement with microsphere treatments at the end of the time course with the modeled data. IHC showed that macrophage infiltration and peroxynitrite-mediated oxidative stress (measured via nitrotyrosine) were present in both saline- and tempo-PPS-treated mice, and the staining was heterogeneous both within tissue sections and within treatment groups (FIG. 23). This heterogeneity warrants further studies with bulk tissue measurements such as a Western blot for nitrotyrosine. Another notable result in these studies is that mice treated with blank PPS microspheres were statistically equivalent to mice treated with tempo-PPS microspheres in the functional endpoints, suggesting that scavenging of $H_2O_2$ and peroxynitrite by PPS is a driving factor in this enhanced response. However, the dose of tempo-benzoate is very low compared to the dose of PPS, so it is difficult to discern whether tempo-benzoate would provide an additive effect using the current formulation. Overall, these microspheres show promise for targeting local oxidative stress and improving the vascular response to ischemia in mice with prolonged hyperglycemia. Future studies could investigate optimization of the relative doses of the PPS and tempo-benzoate components of the dual ROS-scavenging system.

6. Conclusions from Example 2

There is a significant need for improved therapies for diabetic PAD, as two decades of clinical trials have yielded inconsistent outcomes and no new Food and Drug Administration-approved therapies for PAD. In this work, oxidation-sensitive PPS was used to encapsulate a superoxide-scavenging nitroxide radical, tempo-benzoate, in microspheres for local delivery of dual-antioxidant therapy. The microspheres provide environmentally-responsive drug release and are capable of scavenging multiple ROS including $H_2O_2$, superoxide, and peroxynitrite. A mouse model of diabetic PAD with significant oxidative stress and an impaired response to ischemia was identified, and blank PPS and tempo-PPS microspheres were evaluated in vivo. The microspheres were found to reduce ROS levels in muscle tissue when administered at a high dose, while a lower dose was more effective in improving functional measures of vascular recovery in the ischemic hind limb. Interestingly, the blank PPS microspheres provided an equivalent effect to that of the tempo-PPS microspheres in vivo, suggesting that targeting $H_2O_2$ and peroxynitrite in the model is an effective strategy. The results from the current work and prior studies have established the PPS microsphere system as a promising drug delivery vehicle for treatment of diabetic PAD or other pathologies associated with localized oxidative stress.

Example 3

This Example demonstrates an embodiment of the present invention, namely TPCA-1-loaded PPS microspheres for downregulation of MMP-13 in Osteoarthritis.

Osteoarthritis (OA) is a leading cause of chronic disability in the world, and the current methods for treatment are limited. Breakdown of structural collagen in articular cartilage by matrix metalloproteinases (MMPs), especially MMP-1 and MMP-13, is significantly increased in OA. Furthermore, it has been shown that mice deficient in MMP-13 are resistant to surgical induction of OA. NF-kB pathway plays vital role in the catabolic progression during OA. TPCA-1, an anti-inflammatory molecule, is known to inhibit NF-kB.

This example shows the in vivo efficacy of using TPCA-1 (an NF-κB pathway inhibitor) loaded poly(propylene sulfide) microspheres (PPS) to downregulate matrix metalloproteinase-13 (MMP-13) in order to reduce OA progression. For the study, C57BL/6 mice knees were injected with TPCA-1-PPS microspheres, TPCA-1 in its soluble form, or a PBS saline control. The mice were then given loading cycles to induce damage to the knee via the Poulet model of knee overload. At the completion of the loading cycles, the mice were given fluorescent indicators and evaluated using IVIS (in vivo imaging system) for type II collagen (and indicator of cartilage damage), and MMP activity (implicated in the progression of OA). The results of this study show that the use of TPCA-1 loaded PPS microspheres significantly reduced cartilage damage (p=0.0181) as well as MMP activity (p=0.0184) at the time of evaluation. This difference was not seen in the mice given the soluble form of TPCA-1 however. At these results, we conclude that TPCA-1-PPS microspheres are effective at reducing MMP-13 activity and reduce cartilage damage.

Materials/Experimental Animals

TPCA-PPS microspheres were made as shown above. Chondrocytes were obtained from porcine cadavers prepared by the University of Tennessee Heath Science Center. MMPSense750 and XenoFluor 680 was obtained from PerkinElmer. Monoclonal antibodies to type II collagen were produced in our lab. C57BL/6 male mice were obtained from Jackson Laboratory (Maine, USA) and was acclimated in a housing facility before experimentation. A custom fit ElectroForce® 3200 (Bose Corp., Minnesota, USA) biomaterials test instrument was used for mechanical loading. The mechanical loading apparatus was custom made to fit the proximal tibia in the upper cup and dorsiflexed ankle in the bottom cup.

Results

As shown in FIG. 23, TNF-α alone produced an almost 20-fold increase in MMP-13 expression. There was no apparent change when blank PPS was administered. In the testing group with TPCA-1-PPS, there was a significant reduction in MMP-13 expression (p=0.0061).

In Vivo Mouse Study

Figure 24:
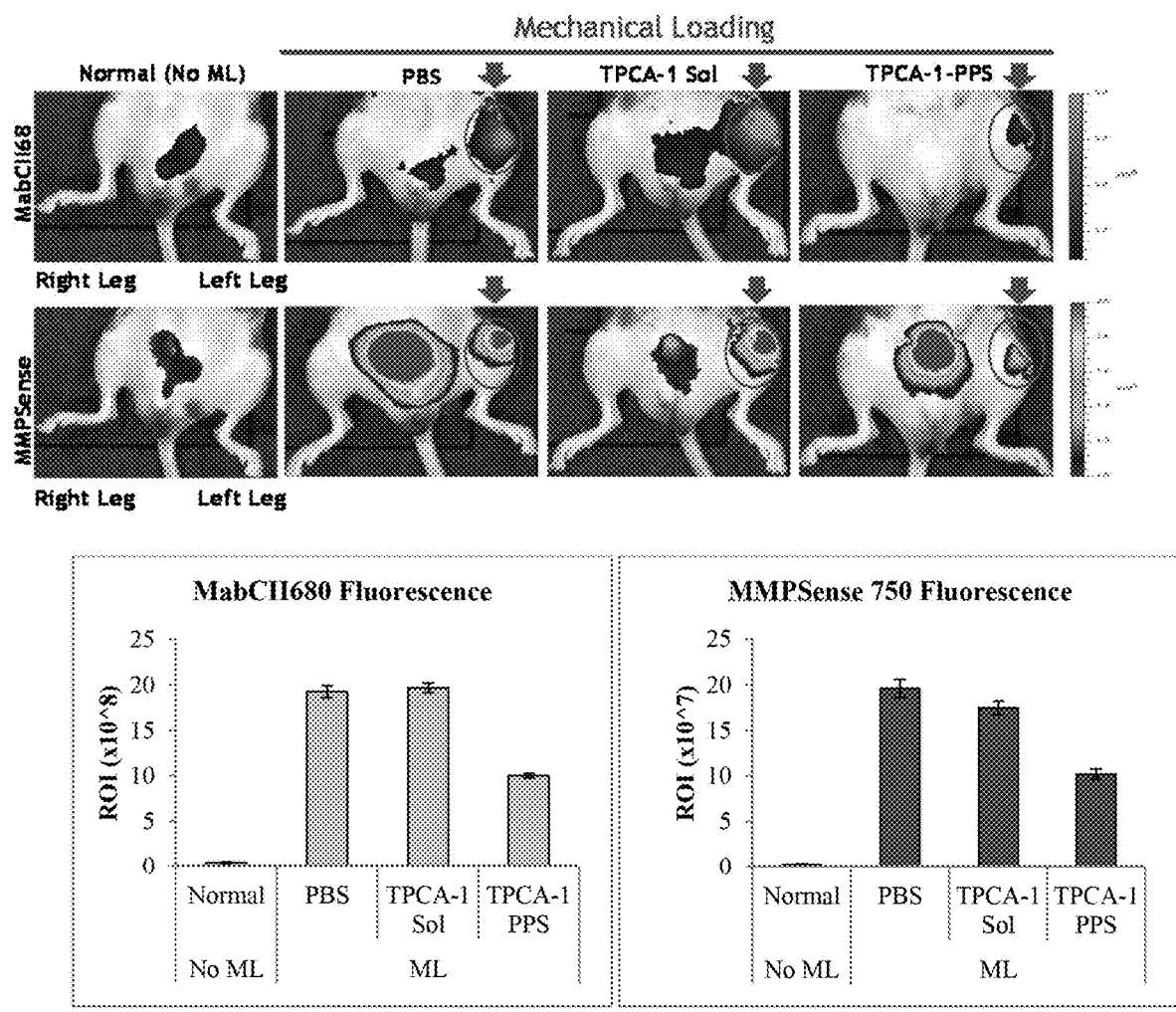
FIG. 24: IVIS images. Note that the mice in the MabCII images do not necessarily correspond to the MMPSense mice. As indicated by both the IVIS images and the bar graphs below, there is no significant difference between the PBS group and the soluble TPCA-1 group. However, there is a significant reduction in both MabCII and MMPSense fluorescence in the TPCA-1-PPS group.

As can be seen in FIG. 24, for mice given the TPCA-1 in solution, there was not a significant reduction in fluorescence in either exposed type II collagen or MMP-13 activity. However, in the TPCA-1 loaded PPS microsphere treatment group there was a significant reduction in fluorescence in both MabCII (p=0.0181) and MMPSense (p=0.0184).

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a protein" includes a plurality of such proteins, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are referenced, including publications, patents, and patent applications. All such references, specifically including the ones listed below, are incorporated herein by reference in their entirety.

REFERENCES

[1] Ross R. Atherosclerosis—an inflammatory disease. New Engl J Med. 1999; 340:115-26.
[2] Stocker R, Keaney J F, Jr. New insights on oxidative stress in the artery wall. J Thromb Haemost: JTH. 2005; 3:1825-34.
[3] Dopheide J F, Doppler C, Scheer M, Obst V, Radmacher M C, Radsak M P, et al. Critical limb ischaemia is characterised by an increased production of whole blood reactive oxygen species and expression of TREM-1 on neutrophils. Atherosclerosis. 2013; 229:396-403.
[4] Pu H L, Chiang W L, Maiti B, Liao Z X, Ho Y C, Shim M S, et al. Nanoparticles with dual responses to oxidative stress and reduced ph for drug release and anti-inflammatory applications. ACS Nano. 2014; 8:1213-21.
[5] Grisham M B, Granger D N, Lefer D J. Modulation of leukocyte-endothelial interactions by reactive metabolites of oxygen and nitrogen: relevance to ischemic heart disease. Free Radical Bio Med. 1998; 25:404-33.
[6] Wang Q, Tang X N, Yenari M A. The inflammatory response in stroke. J Neuroimmunol. 2007; 184:53-68.
[7] Hink U, Li H, Mollnau H, Oelze M, Matheis E, Hartmann M, et al. Mechanisms underlying endothelial dysfunction in diabetes mellitus. Circ Res. 2001; 88:E14-22.
[8] Brownlee M. Biochemistry and molecular cell biology of diabetic complications. Nature. 2001; 414:813-20.
[9] Giugliano D, Ceriello A, Paolisso G. Oxidative stress and diabetic vascular complications. Diabetes Care. 1996; 19:257-67.
[10] Kojda G, Harrison D. Interactions between NO and reactive oxygen species: pathophysiological importance in atherosclerosis, hypertension, diabetes and heart failure. Cardiovasc Res. 1999; 43:562-71.
[11] Petznick A M, Shubrook J H. Treatment of specific macrovascular beds in patients with diabetes mellitus. Osteopath Med Prim Care. 2010; 4:5.
[12] Steffen L M, Duprez D A, Boucher J L, Ershow A G, Hirsch A T. Management of Peripheral Arterial Disease. Diabetes Spectr. 2008; 21:171-7.
[13] Peripheral arterial disease in people with diabetes. Diabetes Care. 2003; 26:3333-41.
[14] Jude E B, Oyibo S O, Chalmers N, Boulton A J. Peripheral arterial disease in diabetic and nondiabetic patients: a comparison of severity and outcome. Diabetes Care. 2001; 24:1433-7.
[15] Ebrahimian T G, Heymes C, You D, Blanc-Brude O, Mees B, Waeckel L, et al. NADPH oxidase-derived overproduction of reactive oxygen species impairs postischemic neovascularization in mice with type 1 diabetes. Am J Pathol. 2006; 169:719-28.
[16] Ceradini D J, Yao D, Grogan R H, Callaghan M J, Edelstein D, Brownlee M, et al. Decreasing intracellular superoxide corrects defective ischemia-induced new vessel formation in diabetic mice. J Biol Chem. 2008; 283:10930-8.
[17] Rivard A, Silver M, Chen D, Kearney M, Magner M, Annex B, et al. Rescue of diabetesrelated impairment of angiogenesis by intramuscular gene therapy with adeno-VEGF. Am J Pathol. 1999; 154:355-63.
[18] Joe B, Vijaykumar M, Lokesh B R. Biological properties of curcumin-cellular and molecular mechanisms of action. Crc Cr Rev Food Sci. 2004; 44:97-111.
[19] Singh S, Aggarwal B B. Activation of transcription factor N F-kappa B is suppressed by curcumin (diferuloylmethane) [corrected]. J Biol Chem. 1995; 270:24995-5000.
[20] Barzegar A, Moosavi-Movahedi A A. Intracellular ROS protection efficiency and free radical-scavenging activity of curcumin. PLOS One. 2011; 6:e26012.
[21] Avci G, Kadioglu H, Sehirli A O, Bozkurt S, Guclu O, Arslan E, et al. Curcumin protects against ischemia/reperfusion injury in rat skeletal muscle. J Surg Res. 2012; 172:e39-46.
[22] Rogers N M, Stephenson M D, Kitching A R, Horowitz J D, Coates P T. Amelioration of renal ischaemia-reperfusion injury by liposomal delivery of curcumin to renal tubular epithelial and antigen-presenting cells. Brit J Pharmacol. 2012; 166:194-209.

[23] Anand P, Kunnumakkara A B, Newman R A, Aggarwal B B. Bioavailability of curcumin: problems and promises. Mol Pharm. 2007; 4:807-18.

[24] Altunbas A, Lee S J, Rajasekaran S A, Schneider J P, Pochan D J. Encapsulation of curcumin in self-assembling peptide hydrogels as injectable drug delivery vehicles. Biomaterials. 2011; 32:5906-14.

[25] Sun D, Zhuang X, Xiang X, Liu Y, Zhang S, Liu C, et al. A novel nanoparticle drug delivery system: the anti-inflammatory activity of curcumin is enhanced when encapsulated in exosomes. Mol Ther. 2010; 18:1606-14.

[26] Shahani K, Swaminathan S K, Freeman D, Blum A, Ma L, Panyam J. Injectable sustained release microparticles of curcumin: a new concept for cancer chemoprevention. Cancer Res. 2010; 70:4443-52.

[27] Zhu G, Mallery S R, Schwendeman S P. Stabilization of proteins encapsulated in injectable poly (lactide-coglycolide). Nat Biotechnol. 2000; 18:52-7.

[28] Vert M, Li S, Garreau H. More About the Degradation of La/Ga-Derived Matrices in Aqueous-Media. J Control Release. 1991; 16:15-26.

[29] Jeffery H, Davis S S, Ohagan D T. The Preparation and Characterization of Poly(Lactide-Co-Glycolide) Microparticles 0.1. Oil-in-Water Emulsion Solvent Evaporation. Int J Pharm. 1991; 77:169-75.

[30] Napoli A, Valentini M, Tirelli N, Muller M, Hubbell J A. Oxidation-responsive polymeric vesicles. Nat Mater. 2004; 3:183-9.

[31] Reddy S T, Rehor A, Schmoekel H G, Hubbell J A, Swartz M A. In vivo targeting of dendritic cells in lymph nodes with poly(propylene sulfide) nanoparticles. J Control Release. 2006; 112:26-34.

[32] Hu P, Tirelli N. Scavenging ROS: superoxide dismutase/catalase mimetics by the use of an oxidation-sensitive nanocarrier/enzyme conjugate. Bioconjugate Chem. 2012; 23:438-49.

[33] Velluto D, Demurtas D, Hubbell J A. PEG-b-PPS diblock copolymer aggregates for hydrophobic drug solubilization and release: cyclosporin A as an example. Mol Pharm. 2008; 5:632-42.

[34] Gupta M K, Meyer T A, Nelson C E, Duvall C L. Poly(PS-b-DMA) micelles for reactive oxygen species triggered drug release. J Control Release. 2012; 162:591-8.

[35] Gupta M K, Martin J R, Werfel T A, Shen T, Page J M, Duvall C L. Cell Protective, ABC triblock polymer-based thermoresponsive hydrogels with ROS-triggered degradation and drug release. J Am Chem Soc. 2014; 136:14896-902.

[36] Purcell B P, Lobb D, Charati M B, Dorsey S M, Wade R J, Zellars K N, et al. Injectable and bioresponsive hydrogels for on-demand matrix metalloproteinase inhibition. Nat Mater. 2014; 13:653-61.

[37] Wilson D S, Dalmasso G, Wang L, Sitaraman S V, Merlin D, Murthy N. Orally delivered thioketal nanoparticles loaded with TNF-alpha-siRNA target inflammation and inhibit gene expression in the intestines. Nat Mater. 2010; 9:923-8.

[38] Lee D, Bae S, Hong D, Lim H, Yoon J H, Hwang O, et al. H2O2-responsive molecularly engineered polymer nanoparticles as ischemia/reperfusion-targeted nanotherapeutic agents. Sci Rep. 2013; 3:2233.

[39] Poole K M, Tucker-Schwartz J M, Sit W W, Walsh A J, Duvall C L, Skala M C. Quantitative optical imaging of vascular response in vivo in a model of peripheral arterial disease. Am J Physiol-Heart C. 2013; 305:H1168-80.

[40] Convertine A J, Benoit D S, Duvall C L, Hoffman A S, Stayton P S. Development of a novel endosomolytic diblock copolymer for siRNA delivery. J Control Release. 2009; 133:221-9.

[41] Nagai A, Koike N, Kudo H, Nishikubo T. Controlled Thioacyl Group Transfer (TAGT) Polymerization of Cyclic Sulfide: Novel Approach to A B Diblock Copolymers by the Combination of RAFT and TAGT Polymerizations. Macromolecules. 2007; 40:8129-31.

[42] Fundueanu G, Constantin M, Stanciu C, Theodoridis G, Ascenzi P. pH- and temperaturesensitive polymeric microspheres for drug delivery: the dissolution of copolymers modulates drug release. J Mater Sci-Mater M. 2009; 20:2465-75.

[43] Hogg N, Darley-Usmar V M, Wilson M T, Moncada S. Production of hydroxyl radicals from the simultaneous generation of superoxide and nitric oxide. Biochem J. 1992; 281 (Pt 2):419-24.

[44] Kuzkaya N, Weissmann N, Harrison D G, Dikalov S. Interactions of peroxynitrite, tetrahydrobiopterin, ascorbic acid, and thiols: implications for uncoupling endothelial nitricoxide synthase. J Biol Chem. 2003; 278:22546-54.

[45] Joshi R V, Nelson C E, Poole K M, Skala M C, Duvall C L. Dual pH- and temperatureresponsive microparticles for protein delivery to ischemic tissues. Acta Biomater. 2013; 9:6526-34.

[46] Lorsbach R B, Murphy W J, Lowenstein C J, Snyder S H, Russell S W. Expression of the Nitric-Oxide Synthase Gene in Mouse Macrophages Activated for Tumor-Cell Killing—Molecular-Basis for the Synergy between Interferon-Gamma and Lipopolysaccharide. J Biol Chem. 1993; 268:1908-13.

[47] Mosser D M, Edwards J P. Exploring the full spectrum of macrophage activation. Nat Rev Immunol. 2008; 8:958-69.

[48] Like A A, Rossini A A. Streptozotocin-induced pancreatic insulitis: new model of diabetes mellitus. Science. 1976; 193:415-7.

[49] Couffinhal T, Silver M, Zheng L P, Kearney M, Witzenbichler B, Isner J M. Mouse model of angiogenesis. Am J Pathol. 1998; 152:1667-79.

[50] Poole K M, Patil C A, Nelson C E, McCormack D R, Madonna M C, Duvall C L, et al. Longitudinal study of arteriogenesis with swept source optical coherence tomography and hyperspectral imaging. SPIE Photonics West. San Francisco, Calif.: SPIE; 2014. p. 89341Z-Z-7.

[51] Kundu K, Knight S F, Willett N, Lee S, Taylor W R, Murthy N. Hydrocyanines: a class of fluorescent sensors that can image reactive oxygen species in cell culture, tissue, and in vivo. Angew Chem Int Edit. 2009; 48:299-303.

[52] Palmer G M, Fontanella A N, Shan S, Hanna G, Zhang G, Fraser C L, et al. In vivo optical molecular imaging and analysis in mice using dorsal window chamber models applied to hypoxia, vasculature and fluorescent reporters. Nat Protoc. 2011; 6:1355-66.

[53] Shonat R D, Wachman E S, Niu W, Koretsky A P, Farkas D L. Near-simultaneous hemoglobin saturation and oxygen tension maps in mouse brain using an AOTF microscope. Biophys J. 1997; 73:1223-31.

[54] Sorg B S, Moeller B J, Donovan O, Cao Y, Dewhirst M W. Hyperspectral imaging of hemoglobin saturation in tumor microvasculature and tumor hypoxia development. J Biomed Opt. 2005; 10:44004.

[55] Poole K M, McCormack D R, Patil C A, Duvall C L, Skala M C. Quantifying the vascular response to ischemia

[56] Mariampillai A, Standish B A, Moriyama E H, Khurana M, Munce N R, Leung M K, et al. Speckle variance detection of microvasculature using swept-source optical coherence tomography. Opt Lett. 2008; 33:1530-2.

[57] Yousefi S, Qin J, Zhi Z, Wang R K. Label-free optical lymphangiography: development of an automatic segmentation method applied to optical coherence tomography to visualize lymphatic vessels using Hessian filters. J Biomed Opt. 2013; 18:86004.

[58] Rosenkranz B, Winkelmann B R, Parnham M J. Clinical pharmacokinetics of molsidomine. Clin Pharmacokinet. 1996; 30:372-84.

[59] Zhang Y M, Wang H, Li J R, Jimenez D A, Levitan E S, Aizenman E, et al. Peroxynitriteinduced neuronal apoptosis is mediated by intracellular zinc release and 12-lipoxygenase activation. J Neurosci. 2004; 24:10616-27.

[60] Amoli M M, Mousavizadeh R, Sorouri R, Rahmani M, Larijani B. Curcumin inhibits in vitro MCP-1 release from mouse pancreatic islets. Transplant P. 2006; 38:3035-8.

[61] Wang Y, Rangan G K, Goodwin B, Tay Y C, Harris D C. Lipopolysaccharide-induced MCP-1 gene expression in rat tubular epithelial cells is nuclear factor-kappaB dependent. Kidney Int. 2000; 57:2011-22.

[62] Tojo T, Ushio-Fukai M, Yamaoka-Tojo M, Ikeda S, Patrushev N, Alexander R W. Role of gp91(phox) (Nox2)-containing NAD(P)H oxidase in angiogenesis in response to hindlimb ischemia. Circulation. 2005; 111:2347-55.

[63] Wang Y J, Pan M H, Cheng A L, Lin L I, Ho Y S, Hsieh C Y, et al. Stability of curcumin in buffer solutions and characterization of its degradation products. J Pharmaceut Biomed. 1997; 15:1867-76.

[64] O'Toole M G, Henderson R M, Soucy P A, Fasciotto B H, Hoblitzell P J, Keynton R S, et al. Curcumin encapsulation in submicrometer spray-dried chitosan/Tween 20 particles. Biomacromolecules. 2012; 13:2309-14.

[65] Shahani K, Panyam J. Highly loaded, sustained-release microparticles of curcumin for chemoprevention. J Pharm Sci. 2011; 100:2599-609.

[66] May R C, Machesky L M. Phagocytosis and the actin cytoskeleton. J Cell Sci. 2001; 114:1061-77.

[67] Shive M S, Anderson J M. Biodegradation and biocompatibility of PLA and PLGA microspheres. Adv Drug Deliver Rev. 1997; 28:5-24.

[68] Champion J A, Walker A, Mitragotri S. Role of particle size in phagocytosis of polymeric microspheres. Pharm Res. 2008; 25:1815-21.

[69] Hirosue S, Kourtis I C, van der Vlies A J, Hubbell J A, Swartz M A. Antigen delivery to dendritic cells by poly(propylene sulfide) nanoparticles with disulfide conjugated peptides: Cross-presentation and T cell activation. Vaccine. 2010; 28:7897-906.

[70] Rhee S G. Cell signaling. H2O2, a necessary evil for cell signaling. Science. 2006; 312:1882-3.

[71] Hood E D, Chorny M, Greineder C F, I S A, Levy R J, Muzykantov V R. Endothelial targeting of nanocarriers loaded with antioxidant enzymes for protection against vascular oxidative stress and inflammation. Biomaterials. 2014; 35:3708-15.

[72] Derochette S, Franck T, Mouithys-Mickalad A, Deby-Dupont G, Neven P, Serteyn D. Intraand extracellular antioxidant capacities of the new water-soluble form of curcumin (NDS27) on stimulated neutrophils and HL-60 cells. Chem-Biol Interact. 2013; 201:49-57.

[73] Kim H W, Lin A, Guldberg R E, Ushio-Fukai M, Fukai T. Essential role of extracellular SOD in reparative neovascularization induced by hindlimb ischemia. Circ Res. 2007; 101:409-19.

[74] Urao N, Inomata H, Razvi M, Kim H W, Wary K, McKinney R, et al. Role of nox2-based NADPH oxidase in bone marrow and progenitor cell function involved in neovascularization induced by hindlimb ischemia. Circ Res. 2008; 103:212-20.

We claim:

1. A reactive oxygen species scavenging emulsion, the emulsion comprising an injectable pharmaceutically acceptable composition and a polymeric microsphere for targeted delivery to a site with elevated reactive oxygen species;
   wherein the polymer of the polymeric microsphere consists of poly(propylene sulfide); and
   wherein the microsphere has a diameter of at least 0.5 µm.

2. The emulsion of claim 1, wherein the microsphere is loaded with a biologically active agent.

3. The emulsion of claim 2, wherein the biologically active agent is at least one of an enzyme, organic catalyst, antibiotic, antioxidant, anti-reactive oxygen species (ROS) agent, anti-inflammatory, protein, glycoprotein, peptide, polyamino acid, antibody, epitopes of antibodies, nucleic acid, steroidal molecule, antiviral, antirejection agent, immunosuppressant, cytokine, carbohydrate, pharmaceutical, cell, virus, single chain fragment, siRNA, miRNA against the p53/MAP kinase pathway, virus vector, prion, anti-proliferative agents, anti-migratory agents, biologically active polymers, and combinations thereof.

4. The emulsion of claim 2, wherein the biologically active agent is curcumin.

5. The emulsion of claim 2, wherein the biologically active agent is anti-reactive oxygen species (ROS) agents.

6. The emulsion of claim 2, wherein the biologically active agent is superoxide dismutase mimetic 4-hydroxy-TEMPO benzoate.

7. The emulsion of claim 2, wherein the biologically active agent is an NF-κB pathway inhibitor.

8. The emulsion of claim 7, wherein the NF-κB pathway inhibitor is TPCA-1.

9. The emulsion of claim 2, wherein the biologically active agent is hydrophobic.

10. The emulsion of claim 1, wherein the emulsion comprises at least one of an antioxidant, buffer, bacteriostat, bacterial antibiotic, or a combination thereof.

11. The emulsion of claim 1, wherein the microsphere is about 0.5 µm to about 1.5 µm in diameter.

12. The emulsion of claim 1, wherein the microsphere is about 1 µm to about 5 µm in diameter.

13. A method of treating inflammation-related pathologies in a patient in need thereof, comprising:
   administering an inflammation-reducing effective amount of an emulsion, the emulsion comprising an injectable pharmaceutically acceptable composition and a polymeric microsphere for targeted delivery to a site with elevated reactive oxygen species, wherein the polymer of the polymeric microsphere consists of poly(propylene sulfide);
   wherein the microsphere has a diameter of at least 0.5 µm and
   wherein the microsphere is loaded with a biologically active agent.

14. The method of claim 13, further comprising, prior to the administration step, identifying an inflammation site in the patient, and locally injecting the emulsion at the inflammation site.

15. The method of claim 13, wherein the biologically active agent is at least one of an enzyme, organic catalyst, antibiotic, antioxidant, anti-reactive oxygen species (ROS) agent, anti-inflammatory, protein, glycoprotein, peptide, polyamino acid, antibody, epitopes of antibodies, nucleic acid, steroidal molecule, antiviral, antirejection agent, immunosuppressant, cytokine, carbohydrate, pharmaceutical, cell, virus, single chain fragment, siRNA, miRNA against the p53/MAP kinase pathway, virus vector, prion, anti-proliferative agents, anti-migratory agents, biologically active polymers, and combinations thereof.

16. The method of claim 13, wherein the biologically active agent is curcumin, TPCA-1, superoxide dismutase mimetic 4-hydroxy-TEMPO benzoate.

17. A method of locally delivering an anti-inflammatory agent to a subject in need thereof, comprising:
   identifying a site of oxidative stress and/or identifying an inflammation site;
   administering a reactive oxygen species (ROS) scavenging effective amount of the emulsion of claim 1 to the site to locally treat the inflammation;
   wherein the microsphere is loaded with a biologically active agent.

18. The method of claim 17, wherein the emulsion is loaded with curcumin.

19. A method of locally delivering an anti-peripheral artery disease agent to a subject in need thereof, comprising:
   identifying an inflammation site;
   administering a reactive oxygen species (ROS) scavenging effective amount of the emulsion of claim 1 to the site to locally treat peripheral artery disease;
   wherein the microsphere is loaded with a biologically active agent.

20. The method of claim 19, wherein the emulsion is loaded with curcumin.

21. A method of locally treating osteoarthritis to a subject in need thereof, comprising:
   identifying an osteoarthritis site;
   administering an effective cartilage damage reducing amount of the emulsion of claim 1 to the site to locally treat the osteoarthritis;
   wherein the microsphere is loaded with a biologically active agent.

22. The method of claim 21, wherein the emulsion is loaded with TPCA-1.

* * * * *